(12) United States Patent
Zaichik et al.

(10) Patent No.: US 10,386,378 B2
(45) Date of Patent: Aug. 20, 2019

(54) METHOD OF DIAGNOSING PROSTATE CANCER BY DETECTING CHEMICAL ELEMENTS

(71) Applicant: Cambridge Oncometrix Limited, Suffolk (GB)

(72) Inventors: Sofia Zaichik, Chicago, IL (US); Maxim Rossmann, Suffolk (GB); Dmitry Solovyev, Suffolk (GB); Mikhail Lomonosov, Cambridgeshire (GB); Vladimir Zaychik, Kaluga (RU)

(73) Assignee: CAMBRIDGE ONCOMETRIX LIMITED, Suffolk (GB)

( * ) Notice: Subject to any disclaimer, the term of this patent is extended or adjusted under 35 U.S.C. 154(b) by 0 days.

(21) Appl. No.: 15/312,422

(22) PCT Filed: May 19, 2015

(86) PCT No.: PCT/GB2015/051472
§ 371 (c)(1),
(2) Date: Nov. 18, 2016

(87) PCT Pub. No.: WO2015/177536
PCT Pub. Date: Nov. 26, 2015

(65) Prior Publication Data
US 2017/0089930 A1 Mar. 30, 2017

(30) Foreign Application Priority Data
May 19, 2014 (GB) .................................... 1408875.1

(51) Int. Cl.
*G01N 33/84* (2006.01)
*G01N 33/574* (2006.01)

(52) U.S. Cl.
CPC ....... *G01N 33/84* (2013.01); *G01N 33/57434* (2013.01); *G01N 2800/342* (2013.01); *G01N 2800/7028* (2013.01)

(58) Field of Classification Search
CPC ............. G01N 33/84; G01N 33/57434; G01N 2800/7028; G01N 2800/342
See application file for complete search history.

(56) References Cited

U.S. PATENT DOCUMENTS

2004/0229300 A1  11/2004  Frederickson
2007/0292900 A1  12/2007  Frederickson et al.
(Continued)

FOREIGN PATENT DOCUMENTS

| EP | 2 597 464 A2 | 5/2013 |
| SU | 997281 | 7/1982 |
| WO | WO 2013/126501 A1 | 8/2013 |

OTHER PUBLICATIONS

Kavanagh (J. Reprod. Fert., 1985, 75:35-41) (Year: 1985).*
(Continued)

*Primary Examiner* — Jeremy C Flinders
(74) *Attorney, Agent, or Firm* — Scully, Scott, Murphy & Presser, P.C.

(57) ABSTRACT

A method of diagnosing a prostate condition in a subject comprises determining, in a sample obtained from a subject, levels of a plurality of constituents selected from the group consisting of Ca, K, Mg, Zn, Ag, Al, Au, B, Ba, Bi, Br, Cd, Ce, Co, Cr, Cs, Cu, Dy, Er, Fe, Gd, Hg, Ho, La, Li, Mn, Na, Nd, Ni, P, Pb, Pr, Rb, S, Sb, Sc, Se, Si, Sm, Sr, Tb, Th, Tl, U, Y, and Zr. A combination of the levels of the plurality of constituents in the sample is compared with a combination of control levels of the same plurality of constituents. A difference between the combinations is indicative of the prostate condition.

7 Claims, 24 Drawing Sheets

(56) References Cited

U.S. PATENT DOCUMENTS

2010/0099195 A1 4/2010 Frederickson
2011/0046204 A1 2/2011 Costello et al.

OTHER PUBLICATIONS

Banas, A. et al., "Correlation of concentrations of selected trace elements with Gleason grade of prostate tissues", J Biol Inorg Chem, (2010), 15;1147-1155.
Costello, LC. et al., "Prostatic fluid electrolyte composition for the screening of prostate cancer: a potential solution to a major problem", Prostate Cancer and Prostatic Diseases, (2009), 12, 17-24.
Heidenreich, A, et al. "Guidelines on Prostate Cancer", European Association of Urology, (2010), 82 pages.
Horwich, A. et al., "Prostate cancer: ESMO Clinical Practice Guidelines for diagnosis, treatment and follow-up", Annals of Oncology, (May 2010), 21 (Supplement 5): v129-133.
Michaelis, M. et al., "Selenoprotein P in seminal fluid is a novel biomarker of sperm quality", Biochemical and Biophysical Research Communications, (2014), 143, pp. 905-910.
Schroeder, F.H. et al., "Screening and Prostate-Cancer Mortality in a Randomized European Study", N Engl J Med, (Mar. 26, 2009), 360; 13, pp. 1320-1328.
Zaichick, S. et al., "Trace elements of normal, benign hypertrophic and cancerous tissues of the Human prostate gland investigated by neutron actiation analysis", Applied Radiation and Isotopes, (2012), 70, pp. 81-87.
Zaichick, S. et al., "INAA application in the age dynamics assessment of Br, Ca, Cl, K, Mg, Mn, and Na content in he normal human prostate", J Radioanal Nucl Chem, (2011), 288; 197-202.
Zaichick, V. Y. et al., "Zinc in the Human Prostate Gland: Normal, Hyperplastic and Cancerous", International Urology and Nephrology, (1997), 29 (5), pp. 565-574.
Zaichick, V., "Nuclear Analytical Methods in Benign Prostatic Hyperplasia and prostate cancer diagnostics", International Seminar on Interaction of Neutrons with Nuclei—May 20, 2013, 28 pages.
Owen, D. H. et al, "A Review of the Physical and Chemical Properties of Human Semen and the Formulation of a Semen Simulant", Journal of Andrology, (Jul./Aug. 2005), vol. 26, No. 4, pp. 459-469.
Zaichick, V.Y. et al., "Zinc Concentration in Human Prostatic Fluid: Normal, Chronic Prostatitis, Adenoma and Cancer", International Urology and Nephrology (1996), 28 (5). pp. 687-694.
International Search report dated Jul. 28, 2015 issued in PCT/GB2015/051472.
GB Search Report dated Oct. 28, 2014 issued in GB Application No. 1408875.1.
Pamela Christudoss, et al, "Zinc status of patients with benign prostatic hyperplasia and prostate carcinoma", Indian Journal of Urology, Jan. 1, 2011, p. 14, vol. 27, No. 1.
Andrey G. Sarafanov, et al, "Analysis of iron, zinc, selenium and cadmium in paraffin-embedded prostate tissue specimens using inductively coupled plasma mass-spectrometry", Journal of Trace Elements in Medicine and Biology, Nov. 1, 2008, pp. 305-314, vol. 22, No. 4, Fischer, New York, NY, US.
Mehmet Yaman, et al, "Comparison of Trace Metal Concentrations in Malign and Benign Human Prostate", Journal of Medicinal Chemistry, Jan. 1, 2005, pp. 630-634, vol. 48, No. 2.
W .M. Kwiatek, et al, "Micro and bulk analysis of prostate tissues classified as hyperplasia", Spectrochimica Acta Part B: Atomic Spectroscopy, Aug. 8, 2007, pp. 707-710, vol. 62, No. 6-7, New York, NY, US, US.
E. B. Cornel, et al, "Characterization of human prostate cancer, benign prostatic hyperplasia and normal prostate by in vitro 1H and 31P magnetic resonance spectroscopy", Journal of Urology, Dec. 1993, pp. 2019-2024. vol. 150 (6).
Wang Z.A et al. "Luminal cells are favored as the cell of origin for prostate cancer." Cell Rep. 2014;8(5):1339-46.

* cited by examiner

METHOD OF DIAGNOSING PROSTATE CANCER BY DETECTING CHEMICAL ELEMENTS

BACKGROUND OF THE INVENTION

Field of the Invention

The present invention relates to a sensitive diagnostic method for establishing a prostate condition.

Description of the Related Art

Prostate cancer (PCa) remains the second most common cancer worldwide for males with an estimated 900,000 new cases diagnosed in 2008 (Ferlay J, et al. Estimates of cancer incidence and mortality in Europe in 2008, European Journal of Cancer, 2010 46:765-781). According to the Cancer Research UK, PCa is the most common cancer in males in the UK, accounting for 41,000 of new cases of cancer in males every year. In 2008-2010 25% of PCa cases in the UK are diagnosed in men under the age of 65 (CancerStats, Incidence 2009—UK, CRUK May 2012).

Prostate cancer normally causes no symptoms until the cancer has grown large enough to put pressure on the urethra. Symptoms can include weak urinal flow, frequent urination, pain when passing urine etc. Due to the fact that benign prostate conditions such as inflammation, infection and benign prostatic hyperplasia are common in men over the age of 50 and produce similar symptoms, discrimination between prostate cancer and benign prostatic conditions presents a challenge to current diagnostic methods. Currently, there is no single, effective screening test to accurately diagnose prostate cancer in men. The most commonly used PCa diagnostic methods today include the serum prostate-specific antigen analysis (PSA), the digital rectal examination (DRA), and the ultrasound-guided prostate biopsy sampling (Horwich A, et al. Prostate cancer: ESMO Clinical Practice Guidelines for diagnosis, treatment and follow-up. Annals of Oncology 21 (Supplement 5): v129-v133, 2010). Despite the years of research the specificity and sensitivity of the PSA based multi-step diagnostic approach is still highly inaccurate. For example, in the European Randomized Study 75.9% of men who underwent a biopsy because of an elevated PSA value had no cancer (Schroeder F, et al. Screening and Prostate-Cancer Mortality in a Randomized European Study, N Engl J Med 2009; 360: 1320). In addition, a needle biopsy is an invasive and painful procedure with side effects such as prostatitis and blood in urine or semen. Also, many men find the DRA and the needle biopsy embarrassing. In addition to high level of false-positive results, smaller tumors can be missed by current methods with fatal consequences because prostate tumors have the potential to suddenly grow and metastasize.

There is constant search for novel biomarkers to improve specificity of PCa detection. For example, one of such biomarkers currently under clinical investigations is the prostate specific non-coding mRNA marker, PCA3, measured in urine sediment obtained after prostatic massage (Heidenreich A, et al. Guidelines on Prostate Cancer, European Association of Urology 2010). So far, however, none of the investigational biomarkers are being used routinely.

Prostate tissue (Zaichick S and Zaichick V, INAA application in the age dynamics assessment of Br, Ca, Cl, K, Mg, Mn, and Na content in the normal human prostate. J Radioanal Nucl Chem 2011; 288:197-202), expressed prostatic secretions (EPS) (Costello L and Franklin R. Prostatic fluid electrolyte composition for the screening of prostate cancer: a potential solution to a major problem. Prostate Cancer Prostatic Dis 2008; 12(1): 17-24) and seminal fluid (Owen D. and Katz D. A Review of the Physical and Chemical Properties of Human Semen and the Formulation of a Semen Simulant. J Androl 2005:26: 459-469) contain unusually high amounts of electrolytes such as K, Na, Zn, Ca, Mg, Cl, Br and others. The reason for the unusually high metal ion content in normal prostate gland and its excretions is not completely understood, but it was shown that decrease in zinc levels in prostate tissue (Zaichick V, et al. SU997281), prostatic fluid (Zaichick V, et al. Zinc concentration in human prostatic fluid: normal, chronic prostatitis, adenoma and cancer. Int Urol Nephrol 1996:28(5): 687-694) and seminal fluid (Frederickson C. US 2004/229300 A1 and US 2010/0099195 A1; and Leslie C. Costello and Renty B. Franklin, US 2011/0046204 A1) can be used to indicate the risk of prostate cancer. Until now this method has not found practical application.

Thus, so far no reliable method has been developed for prostate cancer detection. Therefore there is a need for a rapid and non-invasive routine prostate cancer test, which can detect PCa in asymptomatic men or discriminate between benign and malignant prostatic conditions in patients with prostatic symptoms.

SUMMARY OF THE INVENTION

The invention provides a method of diagnosing a prostate condition, as defined in the independent claims, to which reference should now be made. Advantageous or preferred features are set forth in dependent claims.

According to an aspect of the invention, there may be provided a method of diagnosing a prostate condition in a subject, comprising:

determining, in a sample obtained from a subject, a level of at least one constituent selected from the group consisting of Ag, Al, Au, B, Ba, Bi, Br, Ca, Cd, Ce, Co, Cr, Cs, Cu, Dy, Er, Fe, Gd, Hg, Ho, K, La, Li, Mg, Mn, Na, Nd, Ni, P, Pb, Pr, Rb, S, Sb, Sc, Se, Si, Sm, Sr, Tb, Th, Tl, U, Y, Zn and Zr; and comparing the level of the at least one constituent in the sample with a control level of the same at least one constituent, in which a difference between the level of the at least one constituent in the sample and the control level of the same at least one constituent, is indicative of the prostate condition.

In another aspect of the invention, there may be provided a method of diagnosing a prostate condition in a subject, comprising:

determining, in a sample obtained from a subject, a level of at least one constituent (or first constituent) selected from the group consisting of Ag, Al, Au, B, Ba, Bi, Br, Ca, Cd, Ce, Co, Cr, Cs, Cu, Dy, Er, Fe, Gd, Hg, Ho, K, La, Li, Mg, Mn, Na, Nd, Ni, P, Pb, Pr, Rb, S, Sb, Sc, Se, Si, Sm, Sr, Tb, Th, Tl, U, Y, Zn and Zr; and either (a) comparing a combination of levels of a plurality of constituents from the at least one constituent in the sample (i.e. a sample combination) with a combination of control levels of the same plurality of constituents (i.e. a control combination), or (b) determining a level of at least one further constituent (or second constituent) not selected from the group consisting of Ag, Al, Au, B, Ba, Bi, Br, Ca, Cd, Ce, Co, Cr, Cs, Cu, Dy, Er, Fe, Gd, Hg, Ho, K, La, Li, Mg, Mn, Na, Nd, Ni, P, Pb, Pr, Rb, S, Sb, Sc, Se, Si, Sm, Sr, Tb, Th, Tl, U, Y, Zn and Zr, and comparing a combination of the level of the at least one constituent and the level of the at least one further constituent in the sample (i.e. a sample combination) with a combination of control levels of the same at least one constituent and the same at least one further constituent (i.e. a control combination), in which a difference between the combinations is indicative of the prostate condition.

In a preferred embodiment, the sample is, or comprises, a bodily fluid. The bodily fluid may be blood, blood plasma, urine, prostatic fluid, expressed prostatic secretion or seminal fluid. Preferably, the bodily fluid comprises expressed prostatic secretion or seminal fluid.

Alternatively, the sample may be, or may comprise, a bodily tissue such as prostate tissue. The prostate tissue may be obtained by biopsy.

The at least one constituent may be selected from the group consisting of Ca, K, Mg, Ag, Al, Au, B, Ba, Bi, Br, Cd, Ce, Co, Cr, Cs, Cu, Dy, Er, Fe, Gd, Hg, Ho, La, Li, Mn, Na, Nd, Ni, P, Pb, Pr, Rb, S, Sb, Sc, Se, Si, Sm, Sr, Tb, Th, Tl, U, Y and Zr. This group may be particularly preferable, should the sample be a bodily fluid.

In another preferred embodiment, the at least one constituent is selected from the group consisting of Al, Ba, Bi, Ca, Cu, Fe, K, Mg, Mn, Se, Tb, Th, U, Y and Zn, or is selected from the group consisting of Al, Be, Bi, Ca, Cu, Fe, K, Mg, Mn, Se, Tb, Th, U and Y. Either of these groups may be particularly preferable, should the sample be a bodily fluid.

In an alternative embodiment the at least one constituent is selected from the group consisting of Mn, Al, Ba, Bi, Ca, Mg, K, Se and Cr. This group may be particularly preferable, should the sample be a bodily fluid.

The at least one constituent may be selected from the group consisting of Ca, K, Mg, Al, Au, B, Ba, Bi, Br, Cd, Ce, Cs, Dy, Er, Gd, Ho, La, Li, Na, Nd, Ni, P, Pb, Pr, S, Si, Sm, Sr, Tb, Th, Tl, U, Y and Zr. This group may be particularly preferable, should the sample be a tissue sample.

In another preferred embodiment, the at least one constituent, is selected from the group consisting of Al, Ba, Bi, Ca, Cu, Fe, K, Mg, Mn, Se and Zn, or is selected from the group consisting of Al, Ba, Bi, Ca, Cu, Fe, K, Mg, Mn and Se. Either of these groups may be particularly preferable, should the sample be a tissue sample.

In an alternative embodiment the at least one constituent is selected from the group consisting of Al, Ba, Bi, Ca, Mg and Mn. This group may be particularly preferable, should the sample be a tissue sample.

In an alternative embodiment the at least one constituent is selected from the group consisting of Al, Ba, Bi, Ca, Cd, Cu, Fe, Mg, Mn and Ni.

The combination of constituents may comprise determining one or more ratios. For example, the method may comprise determining a ratio between a first constituent and a second constituent, or between two or more constituents, selected from the group consisting of Ag, Al, Au, B, Ba, Bi, Br, Ca, Cd, Ce, Co, Cr, Cs, Cu, Dy, Er, Fe, Gd, Hg, Ho, K, La, Li, Mg, Mn, Na, Nd, Ni, P, Pb, Pr, Rb, S, Sb, Sc, Se, Si, Sm, Sr, Tb, Th, Tl, U, Y, Zn and Zr.

In preferred embodiments, the method may comprise determining a ratio of a constituent in relation to Ca, or in relation to Zn. Preferred ratios may include Ca/Ba, Ca/Fe, Mg/Al, Ca/Cu, Mg/Cu, Zn/Cu, Zn/Mn, Ca/Mn, Ca/P, Ca/Si, Ca/Sr, or Ca/Al.

Assessing combinations of constituents may comprise comparing relationships between ratios of constituents. For example, a first sample ratio may be calculated between a first constituent and a second constituent. A second sample ratio may be calculated between a first constituent (which may be the same or different from the first constituent of the first ratio) and a second constituent (which may be the same or different from the second constituent of the first ratio). Either the first or second constituent of the second ratio will thus be different from the first ratio. For example, relationships between ratios may include multiples of two or more ratios such as (Ca/Cu)*(Mg/Cu); (Ca/Cu)*(Zn/Cu); or (Mg/Cu)*(Zn/Cu). Such relationships may then be compared with relationships between control ratios of the same constituents.

Combinations of constituents may include ratios between multiples of two or more constituents. As an illustration, this may include (Ca*Mg*Zn)/(Al*Bi*Cu), (Ca*Mg*Zn)/(Mn*Bi*Se) or (Zn*Ca*Mg*Cd)/(Si*Br*Al*Ba).

Combinations of constituents may comprise multiplication of levels of two or more constituents. As an illustration, this may include (Zn*Rb)/10.

In another preferred embodiment, comparing a combination of levels of constituents with a combination of control levels of the same constituents may involve normalized levels of constituents. For example, constituents may be normalized to control or reference levels of the same constituents. For instance, normalization may include dividing a level of constituent with an average (such as a median or a mean) level of the same constituent taken from normal individuals. A normalized amount of a constituent, such as a normalized mass fraction of an element, may be represented by $_n$.

Combinations of normalized levels may be used. As an illustration, this may include $(Ca_n*Cd_n*Co_n*Hg_n*K_n*Mg_n*Na_n*P_n*Rb_n*S_n*Sc_n*Se_n*Zn_n)/(Ag_n*Al_n*Au_n*B_n*Ba_n*Bi_n*Br_n*Ce_n*Cr_n*Cs_n*Cu_n*Dy_n*Er_n*Fe_n*Gd_n*Ho_n*La_n*Li_n*Mn_n*Nd_n*Ni_n*Pb_n*Pr_n*Sb_n*Si_n*Sm_n*Sr_n*Tb_n*Tl_n*U_n*Y_n*Zr_n)$ or $(Ca_n*Cd_n*Co_n*Hg_n*K_n*Mg_n*Na_n*P_n*Rb_n*S_n*Se_n*Zn_n)/(Ag_n*Al_n*Ba_n*Bi_n*Br_n*Ce_n*Cr_n*Cs_n*Cu_n*Li_n*Mn_n*Ni_n*Pb_n*Sb_n*Si_n*Sr_n)$.

In yet another preferred embodiment, combinations of normalized levels of constituents may be used. As an illustration this may include the use of multiplicative indices, such as $(Ca_n*K_n*Mg_n*Rb_n*S_n*Zn_n)/6$ or $(Ca_n*K_n*Mg_n*Zn_n)/4$. This combination may be particularly preferable, should the sample be a bodily fluid.

In another aspect of the invention, combinations of normalized levels of constituents may represent the sum of normalized levels, such as normalized mass fractions. As an illustration an additive index, such as $(Ca_n+K_n+Mg_n+Zn_n)-4$, may be used. This additive combination may be particularly preferable, should the sample be an expressed prostatic secretion.

In an embodiment of the invention, the method may include the step of obtaining a sample from a subject. Determination of levels of constituents in samples from a subject may occur ex vivo or in vitro.

The at least one further (or second) constituent which is not selected from the group consisting of Ag, Al, Au, B, Ba, Bi, Br, Ca, Cd, Ce, Co, Cr, Cs, Cu, Dy, Er, Fe, Gd, Hg, Ho, K, La, Li, Mg, Mn, Na, Nd, Ni, P, Pb, Pr, Rb, S, Sb, Sc, Se, Si, Sm, Sr, Tb, Th, Tl, U, Y, Zn and Zr, may be any chemical element or any chemical substance such as a protein, DNA or RNA, or any other gene derived product.

The prostate condition may be benign prostatic hyperplasia. Preferably, the prostate condition is prostate cancer.

In another aspect of the invention, there may be provided a device for carrying out a method; the method as described in any form above.

One aim of the present invention may be to provide a rapid, specific, non-invasive and sensitive diagnostic method of establishing the condition of prostatic gland, in particular early non-invasive detection of prostate cancer.

In a broad sense, the method is based on determination of the levels of certain chemical elements present in a biological sample from a subject to establish the prostate condition. The obtained levels and/or any ratio between at least one of the obtained levels and the level of any chemical element or any chemical substance such as a protein, DNA or RNA, or any other gene derived product present in the biological sample from the same subject, and/or any combination of said ratios or said levels may be compared to control levels, ratio of the control levels or their combination. Differential presence of the said biomarkers as compared to the control may be indicative of the prostate condition.

In one aspect, there may be provided a device for detection of the levels of certain chemical elements as biomarkers in a biological sample to establish the prostate condition. The obtained levels and/or any ratio between at least one of the obtained levels and the level of any chemical element, chemical substance or protein in the biological sample from the same subject, and/or any combination of said ratios or said levels may be compared to control levels, ratio of the control levels or their combination. Differential presence of the said biomarkers as compared to the control may be indicative of the prostate condition.

In another aspect, there may be provided the use of determination of the levels of certain chemical elements as biomarkers in a biological sample for establishing the prostate condition. The obtained levels and/or any ratio between at least one of the obtained levels and the level of any chemical element, chemical substance or protein in the biological sample from the same subject, and/or any combination of said ratios or said levels may be compared to control levels, ratio of the control levels or their combination. Differential presence of the said biomarkers as compared to the control may be indicative of the prostate condition.

Comparing a level of a constituent with a control level of the constituent, or a combination of levels of constituents with a combination of control levels of the constituents may provide an indication of the presence or absence of a prostate condition.

The method may also relate to a device or tool to establish the prostate condition.

DEFINITIONS

As used herein, the term, "a" or "an" may mean one or more. As used herein in the claim(s), when used in conjunction with the word "comprising", the words "a" or "an" may mean one but it is also consistent with the meaning of "one or more", "at least one", and "one or more than one". Some embodiments of the invention may consist of or consist essentially of one or more elements, method steps, and/or methods of invention. It is contemplated that any method described herein can be implemented with respect to any other method described herein. As used herein "another" or "other" may mean at least a second or more of the same or different claim element or components thereof.

"Biomarker" means a chemical element that is differentially present (i.e., increased or decreased) in a biological sample from a subject or a group of subjects having a first phenotype (e.g., having a disease) as compared to a biological sample from a subject or group of subjects having a second phenotype (e.g., not having the disease). A biomarker is preferably differentially present at a level that is statistically significant (i.e., a p-value less than 0.05 and/or a q-value of less than 0.10 as determined using either Welch's T-test or Wilcoxon's rank-sum Test).

The "level" of one or more biomarkers, or constituents, means the absolute, relative or normalised amount or concentration of the biomarker or constituent in the sample. As used herein "control" or "control level" indicates the level of a biomarker or constituent that is present in a sample without a particular condition, such as a healthy non-cancerous sample, which may be a sample without the prostate condition, or may be a sample with a benign prostate condition, such as benign prostatic hyperplasia. Such "levels" may be tailored to specific techniques that are used to measure levels of biomarkers, or constituents, in biological samples (e.g., ICP-MS, ICP-AES, EXDRF, colorimetric detection, voltammetry etc.), where the levels of biomarkers or constituents may differ based on the specific technique that is used. The method may include measuring mass fraction levels of the constituents.

"Prostate cancer" refers to a disease in which cancer develops in the prostate, a gland in the male reproductive system.

"Benign prostatic hyperplasia" refers to a histologic diagnosis characterized by proliferation of the cellular elements of the prostate, a gland in the male reproductive system.

"Sample" or "biological sample" means biological material isolated from a subject. The biological sample may contain any biological material suitable for detecting the desired biomarkers, and may comprise cellular and/or non-cellular material from the subject. The sample can be isolated from any suitable biological tissue or bodily fluid such as, for example, prostate tissue, blood, blood plasma, urine, prostatic fluid, expressed prostatic secretion or seminal fluid.

"Subject" means any animal, but is preferably a mammal, such as, for example, a human.

"False positive" is a test result that indicates that a subject has a specific disease or condition when the subject actually does not have the disease or condition.

"False negative" is a test result that indicates that a subject does not have a specific disease or condition when the subject actually has the disease or condition.

"True positive" is a test result that indicates that a subject has a specific disease or condition when the subject actually has the disease or condition.

"True negative" is a test result that indicates that a subject does not have a specific disease or condition when the subject actually does not have the disease or condition.

Test sensitivity is calculated using following equation:

$$\text{Sensitivity} = \{(\text{True Positives(TP)}/[\text{TP+False Negatives(FN)}]\} \times 100\%$$

Test specificity is calculated using following equation:

$$\text{Specificity} = \{\text{True Negatives(TN)}/[\text{TN+False Positives(FP)}]\} \times 100\%$$

Test accuracy is calculated using following equation:

$$\text{Accuracy} = [(\text{TP+TN})/(\text{TP+FP+TN+FN})] \times 100\%$$

"Combination" of levels of constituents refers to any mathematical relationship or manipulation between levels of two or more constituents. As described above, this may include a ratio between levels of constituents (or the quotient of constituents), such as Ca/Fe. It may also include a multiple (or product) of ratios, such as $(Ca/Cu)*(Mg/Cu)$, or it may include a ratio (or quotient) between multiples (or products) of the levels of two or more constituents, such as (Ca*Mg*Zn)/(Al*Bi*Cu). The combination may also include the product of the levels of two or more constituents.

Other and further aspects, features, benefits, and advantages of the present invention will be apparent from the following description of the presently preferred embodiments of the invention given for the purpose of disclosure.

BRIEF DESCRIPTION OF THE DRAWINGS

The appended drawings have been included herein so that the cited features, advantages, and objects of the invention will become clear and can be understood in detail. These drawings form a part of the specification. It is to be noted, however, that the appended drawings illustrate preferred embodiments of the invention and should not be considered to limit the scope of the invention.

Figure 1:
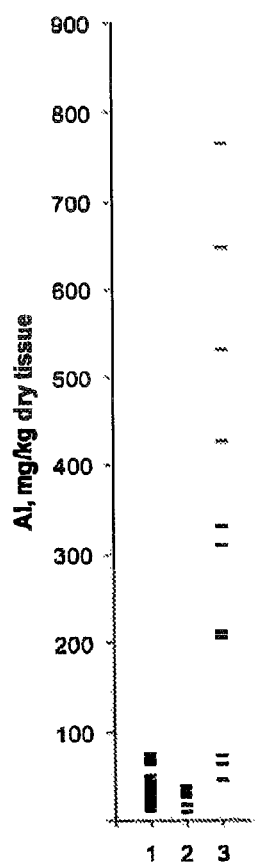
FIG. 1 shows individual data sets for Al mass fractions (mg/kg of dry tissue) in samples of normal (1), benign hyperplastic (2) and cancerous prostate tissue (3).

The following examples are given for the purpose of Illustrating the various embodiments of the present invention and are not meant to limit the present invention in any fashion.

SPECIFIC EXAMPLES

Example 1

Identification of Cancer Biomarkers in Prostate Tissue Using Inductively Coupled Plasma Mass Spectrometry (ICP-MS) and Inductively Coupled Atomic Emission Spectrometry (ICP-AES)

Experimental conditions of the present study were approximated to the hospital conditions as closely as possible.

Equipment:

Autoclave (Ancon-AT2, Russia), inductively coupled plasma mass spectrometry instrument Thermo-Fisher "X-7" (Thermo Electron, USA), Spectrometer ICAP-61 (Thermo Jarrell Ash, USA).

Specimen:

Benign prostate hyperplasla samples (n=43) and prostate adenocarcinoma samples (n=60) were obtained by transrectal biopsy of an indurated site of prostate. Samples of the human normal prostate tissue (n=37) were obtained at autopsy of male patients aged 41-87 died of an injury or in a car accident. The presence or absence of cancer in tissue samples was confirmed by microscopic analysis of tissue morphology.

Reagents:

$HNO_3$ (nitric acid 65% for analysis, max. 0.005 ppm Hg, GR, ISO, Merck), $H_2O_2$ (hydrogen peroxide pure for analysis, Merck), ICP-MS standards ICP-MS-68A and ICP-AM-6-A (High-Purity Standards, Charleston, S.C. 29423, USA), ICP stock solutions (High-Purity Standards, Charleston, S.C. 29423, USA).

Protocol:

1.5 mL of $HNO_3$ and 0.3 mL of $H_2O_2$ were added to homogenized and freeze-dried prostate tissue sample, placed in one-chamber autoclave, and decomposed for 3 hours at 160-200° C. The heat-treated sample was cooled down to the room temperature; the soluble fraction was diluted with deionized water to 20 mL and transferred to a plastic measuring bottle. Simultaneously, the same procedure was performed on a sample containing no prostate tissue, and the resultant solution was used as a blank sample. All samples were analysed by Inductively Coupled Plasma Mass Spectrometry and Inductively Coupled Plasma Atomic Emission Spectrometry.

The spectrometer parameters and the main parameters of ICP-MS measurements: generator output power 1,250 W, spray chamber cooled at 3'C., plasma gas flow rate—12 L/min, nebuliser—Polycon, auxiliary air flow rate—0.9 L/min, nebulizer flow rate—0.9 L/min, sample update—0.8 mL/min, resolution—0.8, detector mode—double, scanning mode—survey scan (number of runs—10, dwell time—0.6 ms, channels per mass—10, acquisition duration—13.2 s) and peak jumping (sweeps—25, dwell time—10 ms, channels per mass—1, acquisition duration—34 s).

The spectrometer parameters for ICP-AES measurements: generator output power 1,200 W, reflected power <5 W, nebuliser type—angular, plasma-forming air flow rate—18/min, auxiliary air flow rate—0.9 L/min, air flow rate into atomiser—0.6 L/min, flow rate of the analysed sample—1.5 mL/min, zone height for plasma observation—14 mm.

Results:

The content of Ag, Al, Au, B, Bi, Br, Cd, Ce, Co, Cr, Cs, Dy, Er, Gd, Hg, Ho, La, Li, Mn, Nd, Ni, Pb, Pr, Rb, Sb, Sc, Se, Si, Sm, Th, Tl, U, Y, and Zr in prostate tissue was analysed by ICP-MS. The content of Na, Mg, P, S, K, Ca, Fe, Cu, Zn, Sr, and Ba in prostate tissue was analysed by ICP-AES.

Statistically significant differences in mass fraction levels of 45 chemical elements (Table 1) were found in samples derived from cancerous, benign hyperplastic and normal prostate tissues. Differences in mass fraction levels of these elements can be used for diagnosis and therapeutic purpose. The data in Table 1 allow evaluating the importance of the individual chemical element content information for the diagnosis of PCa.

TABLE 1

Comparison of mean values (M ± SEM) of chemical element mass fractions (mg · kg$^{-1}$, dry mass basis) in normal, benign hyperplastic (BPH) and cancerous (PCa) prostate tissue

| | Prostate tissue | | | Ratios, p (t-test) | | |
|---|---|---|---|---|---|---|
| Element | Normal 41-87 year n = 37 | BPH 38-83 year n = 43 | PCa 40-79 year n = 60 | BPH to Normal | PCa to Normal | PCa to BPH |
| Ag | 0.0284 ± 0.0035 | 0.0407 ± 0.0088 | 0.255 ± 0.031 | 1.43 | 8.98$^c$ | 6.27$^c$ |
| Al | 34.1 ± 3.5 | 24.4 ± 3.2 | 328 ± 73 | 0.72 | 9.62$^c$ | 13.4$^c$ |
| Au | 0.0041 ± 0.0008 | 0.0026 ± 0.0008 | 0.0297 ± 0.0056 | 0.63 | 7.24$^c$ | 11.4$^c$ |
| B | 1.04 ± 0.18 | 1.51 ± 0.26 | 12.6 ± 3.7 | 1.45 | 12.1$^b$ | 8.34$^b$ |
| Ba | 1.48 ± 0.21 | 1.22 ± 0.20 | 26.7 ± 7.6 | 0.82 | 18.0$^b$ | 21.9$^c$ |
| Bi | 0.029 ± 0.011 | 0.140 ± 0.042 | 1.76 ± 0.27 | 4.83$^a$ | 60.7$^c$ | 16.9$^c$ |
| Br | 27.9 ± 2.9 | 30.0 ± 2.6 | 99.9 ± 8.9 | 1.08 | 3.58$^c$ | 3.33$^c$ |
| Ca | 2397 ± 235 | 2032 ± 165 | 675 ± 58 | 0.85 | 0.28$^c$ | 0.33$^c$ |
| Cd | 1.12 ± 0.12 | 1.07 ± 0.43 | 0.425 ± 0.099 | 0.96 | 0.38$^c$ | 0.40 |
| Ce | 0.0309 ± 0.0050 | 0.0128 ± 0.0019 | 0.101 ± 0.013 | 0.41$^b$ | 3.27$^c$ | 7.89$^c$ |
| Co | 0.0452 ± 0.0043 | 0.0716 ± 0.0097 | 0.0326 ± 0.0037 | 1.58$^a$ | 0.72$^a$ | 0.46$^b$ |
| Cr | 0.53 ± 0.08 | 1.07 ± 0.12 | 2.35 ± 0.37 | 2.02$^c$ | 4.43$^c$ | 2.20$^b$ |
| Cs | 0.0339 ± 0.0033 | 0.0235 ± 0.0025 | 0.0389 ± 0.0039 | 0.69$^a$ | 1.14 | 1.66$^b$ |
| Cu | 9.85 ± 0.97 | 9.86 ± 1.25 | 17.1 ± 2.0 | 1.00 | 1.74$^b$ | 1.74$^b$ |
| Dy | 0.0029 ± 0.0005 | 0.0016 ± 0.0002 | 0.0072 ± 0.0011 | 0.53$^a$ | 2.48$^c$ | 4.50$^c$ |
| Er | 0.00148 ± 0.00023 | 0.00072 ± 0.00013 | 0.00297 ± 0.00038 | 0.49$^b$ | 2.01$^b$ | 4.13$^c$ |
| Fe | 111 ± 9 | 139 ± 10 | 165 ± 15 | 1.25 | 1.49$^a$ | 1.19 |
| Gd | 0.0029 ± 0004 | 0.0015 ± 0.0003 | 0.0094 ± 0.0017 | 0.52$^b$ | 3.24$^c$ | 6.27$^c$ |
| Hg | 0.052 ± 0.009 | 0.275 ± 0.036 | 0.130 ± 0.021 | 5.29$^c$ | 2.50$^c$ | 0.47$^b$ |
| Ho | 0.00057 ± 0.00008 | 0.00032 ± 0.00005 | 0.00178 ± 0.00022 | 0.56$^a$ | 3.12$^c$ | 5.56$^c$ |
| K | 12030 ± 475 | 14472 ± 740 | 8542 ± 504 | 1.20$^b$ | 0.71$^c$ | 0.59$^c$ |
| La | 0.080 ± 0.019 | 0.019 ± 0.003 | 0.970 ± 0.540 | 0.24$^b$ | 12.1 | 51.1 |
| Li | 0.0419 ± 0.0055 | 0.0385 ± 0.0073 | 0.251 ± 0.054 | 0.92 | 5.99$^b$ | 6.52$^a$ |
| Mg | 1071 ± 76 | 1201 ± 83 | 346 ± 61 | 1.12 | 0.32$^c$ | 0.29$^c$ |
| Mn | 1.32 ± 0.08 | 1.19 ± 0.09 | 6.99 ± 1.35 | 0.90 | 5.30$^c$ | 5.87$^c$ |
| Na | 10987 ± 394 | 11612 ± 869 | 7511 ± 643 | 1.06 | 0.68$^c$ | 0.65$^c$ |
| Nd | 0.0137 ± 0.0021 | 0.0062 ± 0.0009 | 0.0413 ± 0.0065 | 0.45$^b$ | 3.01$^c$ | 6.66$^c$ |
| Ni | 3.10 ± 0.51 | 3.22 ± 1.06 | 6.96 ± 1.04 | 1.04 | 2.25$^c$ | 2.16$^b$ |
| P | 7617 ± 368 | 7907 ± 418 | 6675 ± 465 | 1.04 | 0.88 | 0.84 |
| Pb | 2.39 ± 0.56 | 0.69 ± 0.16 | 1.81 ± 0.35 | 0.29$^a$ | 0.76 | 2.62$^b$ |
| Pr | 0.0035 ± 0.0005 | 0.0015 ± 0.0003 | 0.0097 ± 0.0017 | 0.43$^b$ | 2.77$^b$ | 6.47$^c$ |
| Rb | 14.8 ± 0.9 | 14.4 ± 0.7 | 8.8 ± 0.7 | 0.97 | 0.59$^c$ | 0.61$^c$ |
| S | 8557 ± 254 | 8787 ± 487 | 5343 ± 389 | 1.03 | 0.62$^c$ | 0.61$^c$ |
| Sb | 0.037 ± 0.005 | 0.142 ± 0.036 | 0.501 ± 0.062 | 3.84$^b$ | 13.5$^c$ | 3.53$^c$ |
| Sc | 0.0294 ± 0.0053 | 0.0257 ± 0.0040 | 0.0116 ± 0.0015 | 0.87 | 0.39$^b$ | 0.45$^b$ |
| Se | 0.696 ± 0.044 | 1.243 ± 0.079 | 0.576 ± 0.078 | 1.79$^c$ | 0.83 | 0.46$^c$ |
| Si | 102 ± 11 | 141 ± 24 | 284 ± 39 | 1.38 | 2.78$^c$ | 2.02$^b$ |
| Sm | 0.0027 ± 0.0004 | 0.0014 ± 0.0004 | 0.0095 ± 0.0029 | 0.52$^a$ | 3.52$^a$ | 6.71$^b$ |
| Sr | 2.34 ± 0.38 | 3.69 ± 0.45 | 5.75 ± 0.60 | 1.58$^a$ | 2.46$^c$ | 1.56$^a$ |
| Th | 0.0034 ± 0.0007 | 0.0018 ± 0.0003 | 0.0490 ± 0.0120 | 0.52$^a$ | 14.4$^c$ | 27.2$^c$ |
| Tl | 0.0014 ± 0.0002 | 0.0020 ± 0.0006 | 0.0219 ± 0.0056 | 1.43 | 15.6$^c$ | 11.0$^b$ |
| U | 0.0070 ± 0.0021 | 0.0021 ± 0.0009 | 0.0068 ± 0.0013 | 0.30$^a$ | 0.97 | 3.24$^b$ |

TABLE 1-continued

Comparison of mean values (M ± SEM) of chemical element mass fractions (mg · kg$^{-1}$, dry mass basis) in normal, benign hyperplastic (BPH) and cancerous (PCa) prostate tissue

| | Prostate tissue | | | Ratios, p (t-test) | | |
|---|---|---|---|---|---|---|
| Element | Normal<br>41-87 year<br>n = 37 | BPH<br>38-83 year<br>n = 43 | PCa<br>40-79 year<br>n = 60 | BPH<br>to<br>Normal | PCa<br>to<br>Normal | PCa<br>to<br>BPH |
| Y | 0.0186 ± 0.0042 | 0.0071 ± 0.0012 | 0.0340 ± 0.0038 | 0.38[a] | 1.83[b] | 4.79[c] |
| Zn | 1061 ± 153 | 1136 ± 96 | 136 ± 9.9 | 1.07 | 0.13[c] | 0.12[c] |
| Zr | 0.036 ± 0.006 | 0.091 ± 0.036 | 2.13 ± 0.89 | 2.53 | 59.2[a] | 23.4[a] |

M—arithmetic mean,
SEM—standard error of mean,
[a]p ± 0.05,
[b]p ± 0.01,
[c]p ± 0.001.

Example 2

Establishing the Prostate Condition Using Al Mess Fraction in Prostate Tissue Sample The tissue content of Al was found to be significantly different in most cancerous prostate tissues as compared to normal and benign hyperplastic tissues (Example 1, Table 1). Mass fraction of Al in tissue of normal prostate was found to be 34.1±3.5 (SEM) mg/kg, in BPH 24.4±3.2 (SEM) mg/kg, and in PCa 328±73 (SEM) mg/kg on dry mass basis (Table 1). The upper limit for Al mass fraction in dry normal and BPH prostate tissue was determined to be M+2SD or 70 mg/kg on dry mass basis (FIG. 1).

If PCa needs to be discriminated from normal and BPH tissue and if Al content in a prostate biopsy sample prepared and analyzed as described in the Example 1 exceeds 70 mg/kg dry tissue, prostate carcinoma with an accuracy of 82±12% can be diagnosed. The sensitivity and specificity of the Al based test is 97±3% and 94±4%, respectively.

Example 3

Figure 2:
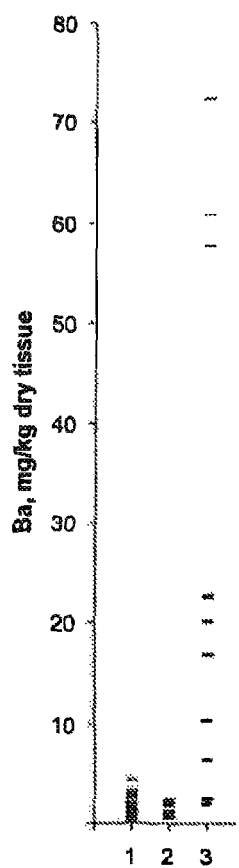
FIG. 2 shows individual data sets for Ba mass fractions (mg/kg of dry tissue) in samples of normal (1), benign hyperplastic (2) and cancerous prostate tissue (3).

Establishing the Prostate Condition Using Ba Mass Fraction in Prostate Tissue Sample The tissue content of Ba was found to be significantly different in most cancerous prostate tissues as compared to normal and benign hyperplastic tissues (Example 1, Table 1). Mass fraction of Ba in tissue of normal prostate was found to be 1.48±0.21 (SEM) mg/kg, in BPH 1.22±0.20 (SEM) mg/kg, and in PCa 26.7±7.6 (SEM) mg/kg on dry mass basis (Table 1). The upper limit for Ba mass fraction in dry normal and BPH prostate tissue was determined to be M+2SD or 3.5 mg/kg on dry mass basis (FIG. 2).

If PCa needs to be discriminated from normal and BPH tissue and if Ba content in a prostate biopsy sample prepared and analyzed as described in the Example 1 exceeds 3.5 mg/kg dry tissue, prostate carcinoma with an accuracy of 82±12% can be diagnosed. The sensitivity and specificity of the Ba based test is 97±3% and 94±4%, respectively.

Example 4

Figure 3:
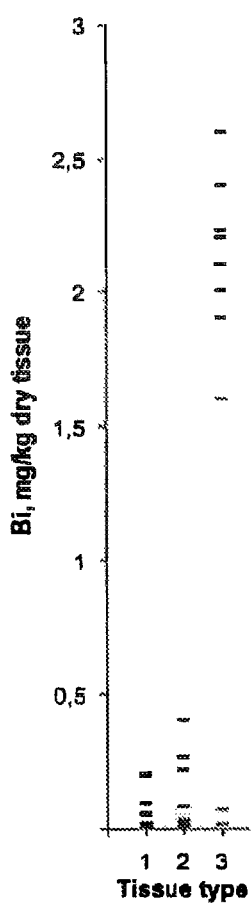
FIG. 3 shows individual data sets for Bi mass fractions (mg/kg of dry tissue) in samples of normal (1), benign hyperplastic (2) and cancerous prostate tissue (3).

Establishing the Prostate Condition Using Bi Mass Fraction in Prostate Tissue Sample The tissue content of Bi was found to be significantly different in most cancerous prostate tissues as compared to normal and benign hyperplastic tissues (Example 1, Table 1). Mass fraction of Bi in tissue of normal prostate was found to be 0.029±0.011 (SEM) mg/kg, in BPH 0.140±0.042 (SEM) mg/kg, and in PCa 1.76±0.27 (SEM) mg/kg on dry mass basis (Table 1). The upper limit for Bi mass fraction in dry normal and BPH prostate tissue was determined to be M+2SD or 0.5 mg/kg on dry mass basis (FIG. 3).

If PCa needs to be discriminated from normal and BPH tissue and if Bi content in a prostate biopsy sample prepared and analyzed as described in the Example 1 exceeds 0.5 mg/kg dry tissue, prostate carcinoma with an accuracy of 82±12% can be diagnosed. The sensitivity and specificity of the Bi based test is 97±3% and 93±4%, respectively.

Example 5

Figure 4:
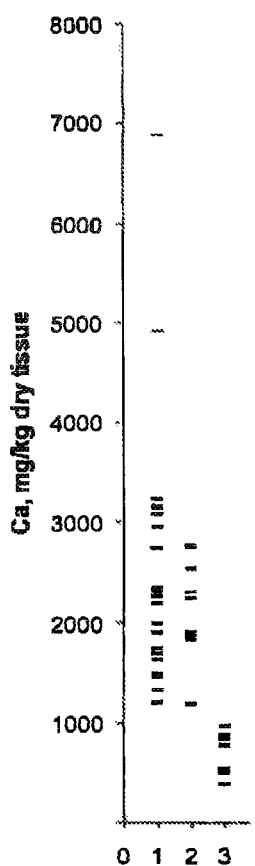
FIG. 4 shows individual data sets for Ca mass fractions (mg/kg of dry tissue) in samples of normal (1), benign hyperplastic (2) and cancerous prostate tissue (3).

Establishing the Prostate Condition Using Ca Mass Fraction in Prostate Tissue Sample The tissue content of Ca was found to be significantly different in most cancerous prostate tissues as compared to normal and benign hyperplastic tissues (Example 1, Table 1). Mass fraction of Ca in tissue of normal prostate was found to be 2397±235 (SEM) mg/kg, in BPH 2032±165 (SEM) mg/kg, and in PCa 675±58 (SEM) mg/kg on dry mass basis (Table 1). The upper limit for Ca mass fraction in dry cancerous prostate tissue was determined to be M+2SD or 1080 mg/kg on dry mass basis (FIG. 4).

If PCa needs to be discriminated from normal and BPH tissue and if Ca content in a prostate biopsy sample prepared and analysed as described in the Example 1 does not exceed 1080 mg/kg dry tissue, prostate carcinoma with an accuracy of 98% can be diagnosed. The sensitivity and specificity of the Ca based test is 98% and 97%, respectively.

Example 6

Figure 5:
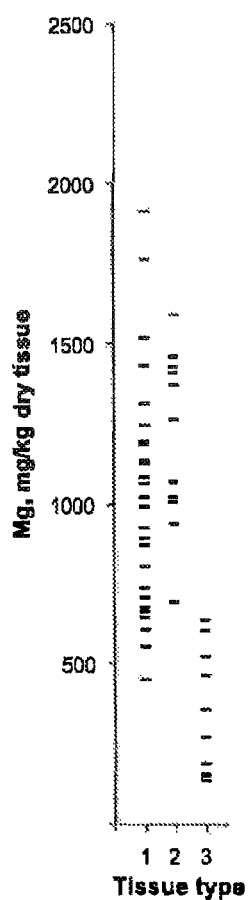
FIG. 5 shows individual data sets for Mg mass fractions (mg/kg of dry tissue) in samples of normal (1), benign hyperplastic (2) and cancerous prostate tissue (3).

Establishing the Prostate Condition Using Mg Mass Fraction in Prostate Tissue Sample The tissue content of Mg was found to be significantly different in most cancerous prostate tissues as compared to normal and benign hyperplastic tissues (Example 1, Table 1). Mass fraction of Mg in tissue of normal prostate was found to be 1071±7 (SEM) mg/kg, in BPH 1201±83 (SEM) mg/kg, and in PCa 346±61 (SEM) mg/kg on dry mass basis (Table 1). The upper limit for Mg mass fraction in dry cancerous prostate tissue was determined to be M+2SD or 700 mg/kg on dry mass basis (FIG. 5).

If PCa needs to be discriminated from normal and BPH tissue and if Mg content in a prostate biopsy sample prepared and analysed as described in the Example 1 does not exceed 700 mg/kg dry tissue, prostate carcinoma with an accuracy of 90±4% can be diagnosed. The sensitivity and specificity of the Mg based test is 100-10% and 84±6%, respectively.

Example 7

Figure 6:
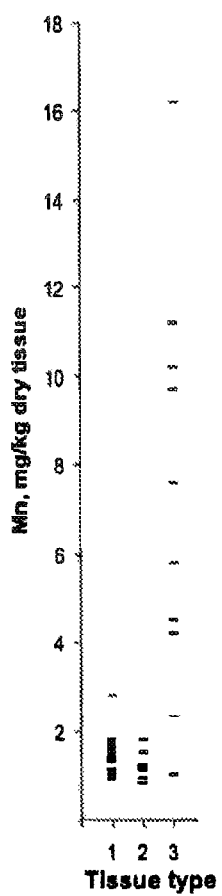
FIG. 6 shows individual data sets for Mn mass fractions (mg/kg of dry tissue) in samples of normal (1), benign hyperplastic (2) and cancerous prostate tissue (3).

Establishing the Prostate Condition Using Mn Mass Fraction in Prostate Tissue Sample The tissue content of Mn was found to be significantly different in most cancerous prostate tissues as compared to normal and benign hyperplastic tissues (Example 1, Table 1). Mass fraction of Mn in tissue of normal prostate was found to be 1.32±0.08 (SEM) mg/kg, in BPH 1.19±0.09 (SEM) mg/kg, and in PCa 6.99±1.35 (SEM) mg/kg on dry mass basis (Table 1). The upper limit for Mn mass fraction in dry normal or BPH prostate tissue was determined to be M+2SD or 2 mg/kg on dry mass basis (FIG. 6).

If PCa needs to be discriminated from normal and BPH tissue and if Mn content in a prostate biopsy sample prepared and analysed as described in the Example 1 exceeds 2 mg/kg dry tissue, prostate carcinoma with an accuracy of 96±3% can be diagnosed. The sensitivity and specificity of the Mn based test is 91±9% and 97±3%, respectively.

Example 8

Determination of Mass Fraction Levels of 44 Elements Relative to the Mass Fraction of Calcium in Normal, Cancerous and BPH Prostate Tissue Mass fraction ratios of the elements mentioned in the Example 1 are different in non-cancerous and cancerous tissue and therefore these can be used as prostate tumor biomarkers. In the Table 2 mass fraction ratios of 44 elements relative to mass fraction of calcium are presented. Further, ratios of the mass fraction ratios for normal prostate tissue, BPH and cancerous tissue are given. The mass fraction ratios presented in the Table 2 is a mean of ratios calculated for every single prostate sample. The data in the Table 2 allow evaluating the importance of individual mass fraction ratios of 44 elements relative to the mass fraction of calcium for the diagnosis of PCa.

TABLE 2

Means of ratios (M ± SEM), their ratios and the reliability of difference between mean values of mass fraction ratios of Ca to mass fractions of other chemical element in normal, benign hyperplastic (BPH) and cancerous (PCa) prostate tissue.

| Mass fraction ratio | Prostate tissue | | | Ratios of means, p (t-test) | | |
|---|---|---|---|---|---|---|
| | Normal 41-79 year n = 37 | BPH 38-83 year n = 43 | PCa 40-79 year n = 60 | BPH to Normal | PCa to Normal | PCa to BPH |
| Ca/Ag | 107037 ± 15763 | 117550 ± 34515 | 4164 ± 1611 | 1.10 | 0.039$^c$ | 0.035$^b$ |
| Ca/Al | 103 ± 21 | 101 ± 18 | 5.24 ± 1.9 | 0.98 | 0.051$^c$ | 0.052$^c$ |
| Ca/B | 4320 ± 805 | 1550 ± 191 | 119 ± 58 | 0.36$^b$ | 0.028$^c$ | 0.077$^c$ |
| Ca/Ba | 2957 ± 577 | 2034 ± 251 | 102 ± 47 | 0.69 | 0.035$^c$ | 0.050$^c$ |
| Ca/Bi | 532698 ± 114578 | 93934 ± 41193 | 7501 ± 6139 | 0.18$^c$ | 0.014$^c$ | 0.080$^a$ |
| Ca/Br | 91.3 ± 12.7 | 78.9 ± 14.6 | 11.1 ± 4.8 | 0.86 | 0.12$^c$ | 0.14$^c$ |
| Ca/Cd | 3085 ± 455 | 3753 ± 732 | 2002 ± 212 | 1.22 | 0.65$^a$ | 0.53$^a$ |
| Ca/Ce | 144087 ± 28909 | 191735 ± 31186 | 8862 ± 2222 | 1.33 | 0.062$^c$ | 0.046$^c$ |
| Ca/Co | 69329 ± 11034 | 42314 ± 4982 | 13669 ± 1072 | 0.61$^a$ | 0.20$^c$ | 0.32$^c$ |
| Ca/Cr | 14516 ± 6572 | 2169 ± 218 | 191 ± 41 | 0.15 | 0.013$^a$ | 0.088$^c$ |
| Ca/Cs | 94882 ± 17335 | 92843 ± 9485 | 22723 ± 6474 | 0.98 | 0.24$^c$ | 0.24$^c$ |
| Ca/Cu | 315 ± 47 | 223 ± 23 | 56 ± 14 | 0.71 | 0.18$^c$ | 0.25$^c$ |
| Ca/Dy | 1733952 ± 444593 | 1685620 ± 327920 | 161389 ± 47689 | 0.97 | 0.093$^c$ | 0.096$^c$ |
| Ca/Er | 2782727 ± 557202 | 3989832 ± 845199 | 296667 ± 64924 | 1.43 | 0.11$^c$ | 0.074$^c$ |
| Ca/Fe | 20.8 ± 2.4 | 17.8 ± 1.9 | 4.81 ± 0.53 | 0.86 | 0.23$^c$ | 0.27$^c$ |
| Ca/Gd | 1489869 ± 334486 | 1726552 ± 327682 | 118454 ± 35677 | 1.16 | 0.080$^c$ | 0.069$^c$ |
| Ca/Hg | 78186 ± 11882 | 9944 ± 1259 | 4445 ± 2330 | 0.13$^c$ | 0.057$^c$ | 0.45$^a$ |
| Ca/Ho | 7482530 ± 1547065 | 8358623 ± 1644445 | 453653 ± 88284 | 1.12 | 0.061$^c$ | 0.054$^c$ |
| Ca/K | 0.227 ± 0.037 | 0.144 ± 0.013 | 0.081 ± 0.008 | 0.63$^a$ | 0.36$^c$ | 0.56$^c$ |
| Ca/La | 105705 ± 19452 | 128328 ± 16885 | 7340 ± 3488 | 1.21 | 0.069$^c$ | 0.057$^c$ |
| Ca/Li | 79700 ± 10834 | 71782 ± 11904 | 5847 ± 2025 | 0.90 | 0.073$^c$ | 0.082$^c$ |
| Ca/Mg | 2.83 ± 0.51 | 1.72 ± 0.12 | 2.58 ± 0.47 | 0.61 | 0.91 | 1.50 |
| Ca/Mn | 2061 ± 325 | 1789 ± 186 | 181 ± 66 | 0.87 | 0.088$^c$ | 0.10$^c$ |
| Ca/Na | 0.236 ± 0.032 | 0.189 ± 0.025 | 0.097 ± 0.014 | 0.80 | 0.41$^c$ | 0.51$^b$ |
| Ca/Ni | 1916 ± 626 | 1028 ± 179 | 123 ± 28 | 0.54 | 0.064$^b$ | 0.12$^c$ |
| Ca/P | 0.348 ± 0.040 | 0.264 ± 0.025 | 0.112 ± 0.020 | 0.76 | 0.32$^c$ | 0.42$^c$ |
| Ca/Pb | 3774 ± 724 | 4461 ± 756 | 556 ± 149 | 1.18 | 0.15$^c$ | 0.12$^c$ |
| Ca/Pr | 1263853 ± 269288 | 2231480 ± 735010 | 112525 ± 35218 | 1.77 | 0.089$^c$ | 0.050$^b$ |
| Ca/Rb | 180 ± 23 | 139 ± 12 | 81.8 ± 7.8 | 0.77 | 0.45$^c$ | 0.59$^c$ |
| Ca/S | 0.308 ± 0.045 | 0.238 ± 0.022 | 0.133 ± 0.016 | 0.77 | 0.43$^c$ | 0.56$^c$ |
| Ca/Sb | 121963 ± 24741 | 49028 ± 20319 | 2784 ± 556 | 0.40$^a$ | 0.023$^c$ | 0.057$^a$ |
| Ca/Sc | 174958 ± 51707 | 76930 ± 10995 | 49945 ± 6858 | 0.44 | 0.29a | 0.65$^a$ |
| Ca/Se | 3604 ± 500 | 2362 ± 296 | 895 ± 168 | 0.66$^a$ | 0.25$^c$ | 0.38$^c$ |
| Ca/Si | 35.7 ± 6.9 | 17.4 ± 2.3 | 3.21 ± 0.88 | 0.49$^a$ | 0.090$^c$ | 0.18$^c$ |
| Ca/Sm | 1695658 ± 438262 | 2939100 ± 810027 | 142073 ± 3759 | 1.73 | 0.084$^b$ | 0.048$^c$ |
| Ca/Sr | 1334 ± 142 | 743 ± 76 | 137 ± 34 | 0.56$^b$ | 0.10$^c$ | 0.18$^c$ |
| Ca/Th | 1703628 ± 375869 | 1499284 ± 275745 | 43707 ± 21300 | 0.88 | 0.026$^c$ | 0.029$^c$ |
| Ca/Tl | 2870569 ± 627543 | 1464103 ± 252751 | 124174 ± 74903 | 0.51$^a$ | 0.043$^c$ | 0.085$^c$ |
| Ca/U | 1122953 ± 182815 | 2061625 ± 434930 | 130793 ± 22073 | 1.84 | 0.12$^c$ | 0.063$^c$ |
| Ca/Y | 414438 ± 116105 | 385834 ± 74931 | 23034 ± 3863 | 0.93 | 0.056$^b$ | 0.060$^c$ |

TABLE 2-continued

Means of ratios (M ± SEM), their ratios and the reliability of difference between mean values of mass fraction ratios of Ca to mass fractions of other chemical element in normal, benign hyperplastic (BPH) and cancerous (PCa) prostate tissue.

| Mass fraction ratio | Prostate tissue | | | Ratios of means, p (t-test) | | |
|---|---|---|---|---|---|---|
| | Normal 41-79 year n = 37 | BPH 38-83 year n = 43 | PCa 40-79 year n = 60 | BPH to Normal | PCa to Normal | PCa to BPH |
| Ca/Zn | 3.89 ± 0.91 | 1.72 ± 0.21 | 5.02 ± 0.41 | 0.44[a] | 1.29 | 2.92[c] |
| Ca/Zr | 135701 ± 31300 | 61766 ± 18949 | 853 ± 238 | 0.46[a] | 0.0063[c] | 0.014[c] |

M—arithmetic mean,
SEM—standard error of mean,
[a] $p \leq 0.05$,
[b] $p \leq 0.01$,
[c] $p \leq 0.001$.

Example 9

Determination of Mass Fraction Levels of 44 Elements Relative to Mass Fraction of Zinc in Normal, Cancerous and BPH Prostate Tissue Mass fraction ratios of the elements mentioned in the Example 1 are different in non-cancerous and cancerous tissue and therefore these can be used as prostate tumor biomarkers. In the Table 3 mass fraction ratios of 44 elements relative to mass fraction of zinc are presented. Further, ratios of the mass fraction ratios for normal prostate tissue, BPH and cancerous tissue are given. The mass fraction ratios presented in the Table 3 is a mean of ratios calculated for every single prostate sample. The data in the Table 3 allow evaluating the importance of individual mass fraction ratios of 44 elements relative to the mass fraction of Zn for the diagnosis of PCa.

TABLE 3

Means of ratios (M ± SEM), their ratios and the reliability of difference between mean values of mass fraction ratios of Zn to mass fractions of other chemical element in normal, benign hyperplastic (BPH) and cancerous (PCa) prostate tissue

| Mass fraction ratio | Prostate tissue | | | Ratios, p (t-test) | | |
|---|---|---|---|---|---|---|
| | Normal 41-79 year n = 37 | BPH 38-83 year n = 43 | PCa 40-79 year n = 60 | BPH to Normal | PCa to Normal | PCa to BPH |
| Zn/Ag | 32271 ± 5360 | 39748 ± 4328 | 723 ± 133 | 1.23 | 0.022[c] | 0.018[c] |
| Zn/Al | 41.3 ± 9.7 | 59.0 ± 9.8 | 1.16 ± 0.52 | 1.43 | 0.028[c] | 0.020[c] |
| Zn/Au | 645790 ± 240530 | 816590 ± 173610 | 19120 ± 12210 | 1.27 | 0.029[b] | 0.023[c] |
| Zn/B | 1974 ± 559 | 1360 ± 417 | 28.8 ± 21.0 | 0.69 | 0.015[b] | 0.021[b] |
| Zn/Ba | 1003 ± 195 | 1373 ± 203 | 30 ± 17 | 1.37 | 0.030[c] | 0.022[c] |
| Zn/Bi | 236160 ± 62300 | 79960 ± 37890 | 2290 ± 2110 | 0.34[a] | 0.0097[c] | 0.029[a] |
| Zn/Br | 39.1 ± 6.2 | 68.8 ± 11.5 | 1.30 ± 0.14 | 1.76[a] | 0.033[c] | 0.019[c] |
| Zn/Ca | 0.449 ± 0.059 | 0.758 ± 0.171 | 0.169 ± 0.027 | 1.69 | 0.38[c] | 0.22[b] |
| Zn/Cd | 39170 ± 11900 | 39100 ± 6460 | 319 ± 59 | 1.00 | 0.0082[c] | 0.0082[c] |
| Zn/Ce | 60330 ± 14060 | 131210 ± 22300 | 2055 ± 899 | 2.17[b] | 0.035[c] | 0.016[c] |
| Zn/Co | 27011 ± 3716 | 20798 ± 3359 | 4293 ± 554 | 0.77 | 0.16[c] | 0.21[c] |
| Zn/Cr | 2654 ± 356 | 1161 ± 156 | 78.1 ± 13.4 | 0.44[c] | 0.029[c] | 0.067[c] |
| Zn/Cs | 37990 ± 8990 | 69050 ± 15160 | 3899 ± 1158 | 1.82 | 0.103[c] | 0.057[c] |
| Zn/Cu | 114 ± 19 | 133 ± 19 | 9.0 ± 2.3 | 1.17 | 0.079[c] | 0.068[c] |
| Zn/Dy | 657590 ± 148330 | 1194200 ± 255540 | 30310 ± 10770 | 1.81 | 0.046[c] | 0.025[c] |
| Zn/Er | 1190700 ± 293660 | 2796660 ± 590750 | 54040 ± 15720 | 2.35[a] | 0.045[c] | 0.019[c] |
| Zn/Fe | 8.8 ± 1.4 | 11.8 ± 1.5 | 0.97 ± 0.11 | 1.34 | 0.11[c] | 0.082[c] |
| Zn/Gd | 624740 ± 158040 | 1190620 ± 240260 | 23210 ± 8250 | 1.91 | 0.037[c] | 0.019[c] |
| Zn/Hg | 27011 ± 3717 | 6490 ± 688 | 1216 ± 115 | 0.24[c] | 0.045[c] | 0.19[c] |
| Zn/Ho | 3128380 ± 766220 | 5591120 ± 958640 | 97340 ± 37950 | 1.79 | 0.031[c] | 0.017[c] |
| Zn/K | 0.086 ± 0.016 | 0.109 ± 0.024 | 0.0135 ± 0.0026 | 1.27 | 0.16[c] | 0.12[c] |
| Zn/La | 61550 ± 25120 | 96666 ± 23120 | 2156 ± 1250 | 1.57 | 0.035[a] | 0.022[c] |
| Zn/Li | 35526 ± 9597 | 51562 ± 11566 | 1248 ± 528 | 1.45 | 0.035[b] | 0.024[c] |
| Zn/Mg | 1.01 ± 0.14 | 1.33 ± 0.35 | 0.38 ± 0.50 | 1.32 | 0.38 | 0.29 |
| Zn/Mn | 847 ± 210 | 1261 ± 185 | 43 ± 23 | 1.49 | 0.051[c] | 0.034[c] |
| Zn/Na | 0.099 ± 0.019 | 0.144 ± 0.035 | 0.0153 ± 0.002 | 1.45 | 0.15[c] | 0.11[b] |
| Zn/Nd | 133860 ± 32890 | 275460 ± 44660 | 4690 ± 1810 | 2.05[a] | 0.035[c] | 0.017[c] |
| Zn/Ni | 712 ± 185 | 820 ± 220 | 26 ± 11 | 1.15 | 0.037[c] | 0.032[c] |
| Zn/P | 0.128 ± 0.016 | 0.198 ± 0.041 | 0.0187 ± 0.0042 | 1.55 | 0.15[c] | 0.094[c] |
| Zn/Pb | 1523 ± 348 | 2910 ± 470 | 128 ± 58 | 1.91[a] | 0.084[c] | 0.044[c] |
| Zn/Pr | 529125 ± 130900 | 1429530 ± 348740 | 21630 ± 7700 | 2.70[a] | 0.041[c] | 0.015[c] |
| Zn/Rb | 71.7 ± 9.0 | 87.4 ± 9.3 | 17.9 ± 2.0 | 1.22 | 0.26[c] | 0.22[c] |
| Zn/S | 0.123 ± 0.025 | 0.182 ± 0.041 | 0.0213 ± 0.0035 | 1.48 | 0.17[c] | 0.12[c] |
| Zn/Sb | 34333 ± 6156 | 10115 ± 2344 | 334 ± 44 | 0.29[c] | 0.0097[c] | 0.033[c] |
| Zn/Sc | 46794 ± 7866 | 39678 ± 3372 | 13157 ± 1624 | 0.85 | 0.28[c] | 0.33[c] |
| Zn/Se | 1548 ± 166 | 886 ± 90 | 270 ± 28 | 0.57[b] | 0.18[c] | 0.30[c] |

TABLE 3-continued

Means of ratios (M ± SEM), their ratios and the reliability of difference between mean values of mass fraction ratios of Zn to mass fractions of other chemical element in normal, benign hyperplastic (BPH) and cancerous (PCa) prostate tissue

| Mass fraction ratio | Prostate tissue | | | Ratios, p (t-test) | | |
|---|---|---|---|---|---|---|
| | Normal 41-79 year n = 37 | BPH 38-83 year n = 43 | PCa 40-79 year n = 60 | BPH to Normal | PCa to Normal | PCa to BPH |
| Zn/Si | 15.8 ± 4.9 | 14.3 ± 4.6 | 0.69 ± 0.33 | 0.91 | 0.044$^c$ | 0.048$^b$ |
| Zn/Sm | 642630 ± 151110 | 1796120 ± 413200 | 27835 ± 9730 | 2.79$^a$ | 0.043$^c$ | 0.015$^c$ |
| Zn/Sr | 561 ± 83 | 641 ± 223 | 22.2 ± 4.7 | 1.14 | 0.040$^c$ | 0.035$^b$ |
| Zn/Th | 721180 ± 196050 | 1041050 ± 219340 | 12010 ± 7530 | 1.44 | 0.017$^c$ | 0.012$^c$ |
| Zn/Tl | 855140 ± 116010 | 877340 ± 132760 | 35010 ± 26220 | 1.03 | 0.041$^c$ | 0.040$^c$ |
| Zn/U | 461270 ± 98980 | 1514290 ± 378280 | 23375 ± 6170 | 3.28$^b$ | 0.050$^c$ | 0.015$^c$ |
| Zr/Y | 171540 ± 52620 | 271240 ± 54800 | 4540 ± 1495 | 1.58 | 0.026$^b$ | 0.017$^c$ |
| Zn/Zr | 49100 ± 9570 | 41930 ± 11960 | 151 ± 58 | 0.85 | 0.0031$^c$ | 0.0036$^c$ |

M—arithmetic mean,
SEM—standard error of mean,
$^a$p ≤ 0.05,
$^b$p ≤ 0.01,
$^c$p ≤ 0.001.

Example 10

Using the Ca/Fe Mass Fraction Ratio to Establish Prostate Condition

Figure 7:
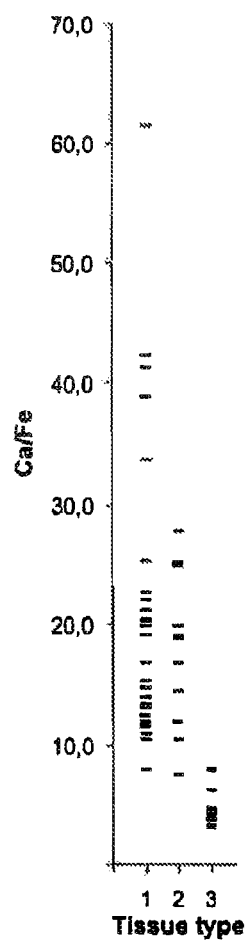
FIG. 7 shows individual data sets for Ca/Fe mass fraction ratio in samples of normal (1), benign hyperplastic (2) and cancerous prostate tissue (3).

The Ca/Fe mass fraction ratio was found to be significantly different in most cancerous prostate tissues as compared to normal and benign hyperplastic tissues (Example 8, Table 2). The upper limit for Ca/Fe mass fraction ratio on dry mass basis in cancerous prostate tissue was determined to be M+3SD (M—arithmetic mean, SD—standard deviation) or 10 (FIG. 7).

If PCa needs to be discriminated from normal and BPH tissue and if the Ca/Fe ratio in a prostate biopsy sample prepared and analysed as described in Example 1 does not exceed 10, prostate carcinoma with an accuracy of 96±3% can be diagnosed. The sensitivity and specificity of the Ca/Fe ratio based test is 100-9% and 95±4%, respectively.

Example 11

Using the Mg/Al Mass Fraction Ratio to Establish Prostate Condition

Figure 8:
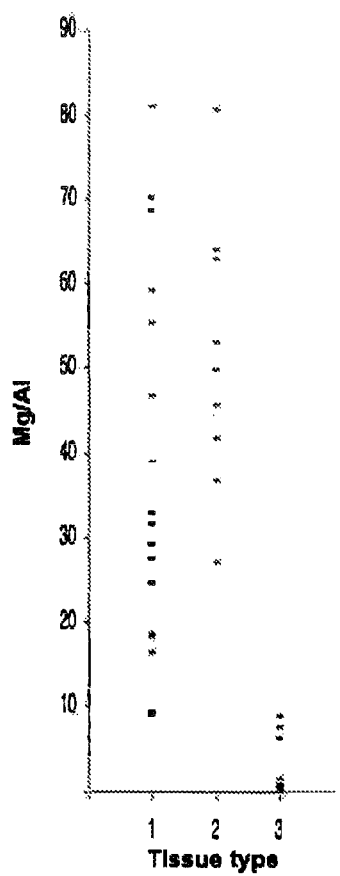
FIG. 8 shows individual data sets for Mg/Al mass fraction ratio in samples of normal (1), benign hyperplastic (2) and cancerous prostate tissue (3).

The Mg/Al mass fraction ratio was found to be significantly different in most cancerous prostate tissues as compared to normal and benign hyperplastic tissues. The upper limit for Mg/Al mass fraction ratio on dry mass basis in cancerous prostate tissue was determined to be M+2SD (M—arithmetic mean, SD—standard deviation) or 9 (FIG. 8).

If PCa needs to be discriminated from normal and BPH tissue and if the Mg/Al ratio in a prostate biopsy sample prepared and analysed as described in Example 1 does not exceed 9, prostate carcinoma with an accuracy of 99% can be diagnosed. The sensitivity and specificity of the Mg/Al ratio based test is 98% and 99%, respectively.

Example 12

Using the Ca/Cu Mass Fraction Ratio to Establish Prostate Condition

Figure 9:
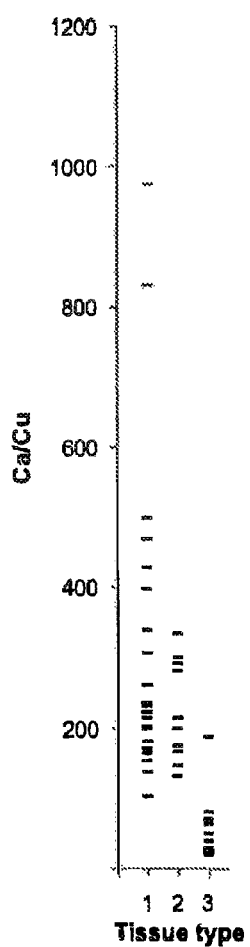
FIG. 9 shows individual data sets for Ca/Cu mass fraction in samples of normal (1), benign hyperplastic (2) and cancerous prostate tissue (3).

The Ca/Cu mass fraction ratio was found to be significantly different in most cancerous prostate tissues as compared to normal and benign hyperplastic tissues (Example 8, Table 2). The upper limit for Ca/Cu mass fraction ratio on dry mass basis in cancerous prostate tissue was determined to be M+3SD (M—arithmetic mean, SD—standard deviation) or 100 (FIG. 9).

If PCa needs to be discriminated from normal and BPH tissue and if the Ca/Cu ratio in a prostate biopsy sample prepared and analysed as described in Example 1 does not exceed 100, prostate carcinoma with an accuracy of 97±3% can be diagnosed. The sensitivity and specificity of the Ca/Cu ratio based test is 91±9% and 100-3%, respectively.

Example 13

Figure 10:
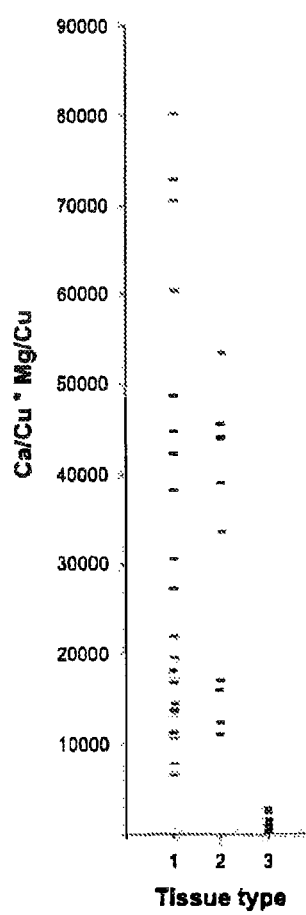
FIG. 10 shows individual data sets for (Ca/Cu)*(Mg/Cu) mass fraction ratios combination in samples of normal (1), benign hyperplastic (2) and cancerous prostate tissue (3).

Using the (Ca/Cu)*(Mg/Cu) Mass Fraction Ratio Combination to Establish Prostate Condition The (Ca/Cu)*(Mg/Cu) mass fraction ratio combination was found to be significantly different in most cancerous prostate tissues as compared to normal and benign hyperplastic tissues. The upper limit for (Ca/Cu)*(Mg/Cu) mass fraction ratio combination on dry mass basis in cancerous prostate tissue was determined to be M+3SD (M—arithmetic mean, SD—standard deviation) or 4000 (FIG. 10).

If PCa needs to be discriminated from normal and BPH tissue and if the (Ca/Cu)*(Mg/Cu) ratio in a prostate biopsy sample prepared and analysed as described in Example 1 does not exceed 4000, prostate carcinoma with an accuracy of 100-2% can be diagnosed. The sensitivity and specificity of the (Ca/Cu)*(Mg/Cu) ratio based test is 100-11% and 100-3%, respectively.

Example 14

Figure 11:
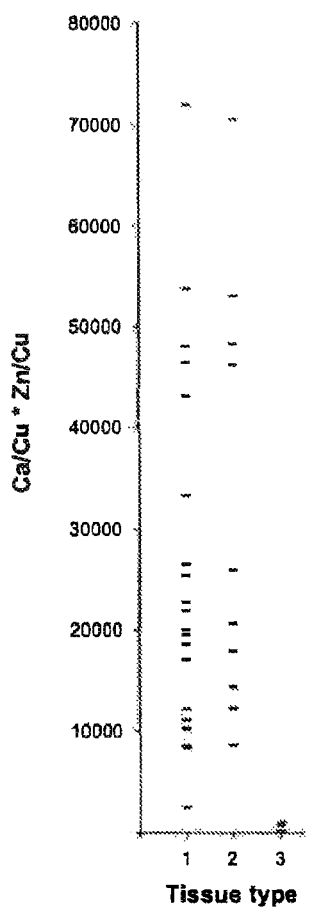
FIG. 11 shows individual data sets for (Ca/Cu)*(Zn/Cu) mass fraction ratios combination in samples of normal (1), benign hyperplastic (2) and cancerous prostate tissue (3).

Using the (Ca/Cu)*(Zn/Cu) Mass Fraction Ratio Combination to Establish Prostate Condition The (Ca/Cu)*(Zn/Cu) mass fraction ratio combination was found to be significantly different in most cancerous prostate tissues as compared to normal and benign hyperplastic tissues. The upper limit for (Ca/Cu)*(Zn/Cu) mass fraction ratio on dry mass basis in cancerous prostate tissue was determined to be M+3SD (M—arithmetic mean, SD—standard deviation) or 1700 (FIG. 11).

If PCa needs to be discriminated from normal and BPH tissue and if the (Ca/Cu)*(Zn/Cu) ratio in a prostate biopsy sample prepared and analysed as described in Example 1 does not exceed 1700, prostate carcinoma with an accuracy of 100-2% can be diagnosed. The sensitivity and specificity of the (Ca/Cu)*(Zn/Cu) ratio based test is 100-10% and 100-3%, respectively.

Example 15

Figure 12:
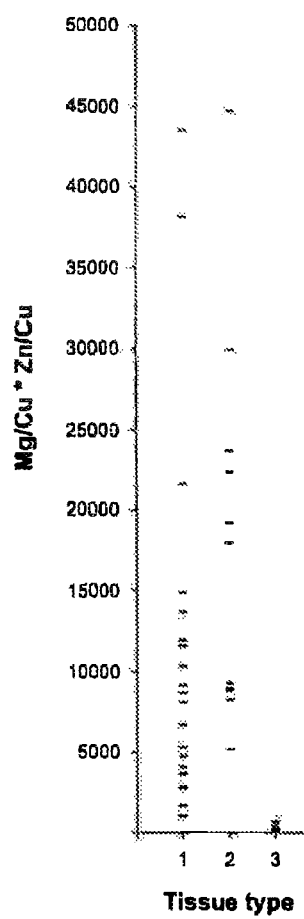
FIG. 12 shows individual data sets for (Mg/Cu)*(Zn/Cu) mass fraction ratios combination in samples of normal (1), benign hyperplastic (2) and cancerous prostate tissue (3).

Using the (Mg/Cu)*(Zn/Cu) Mass Fraction Ratio Combination to Establish Prostate Condition The (Mg/Cu)*(Zn/Cu) mass fraction ratio was found to be significantly different in most cancerous prostate tissues as compared to normal and benign hyperplastic tissues. The upper limit for (Mg/Cu)*(Zn/Cu) mass fraction ratio on dry mass basis in cancerous prostate tissue was determined to be M+3SD (M—arithmetic mean, SD—standard deviation) or 975 (FIG. 12).

If PCa needs to be discriminated from normal and BPH tissue and if the (Mg/Cu)*(Zn/Cu) ratio in a prostate biopsy sample prepared and analysed as described in Example 1 does not exceed 975, prostate carcinoma with an accuracy of 100-2% can be diagnosed. The sensitivity and specificity of the (Mg/Cu)*(Zn/Cu) ratio based test is 100-11% and 100-3%, respectively.

Example 16

Using Bodily Fluids and Tissues to Establish Prostate Condition

Using the method of analysis described in the Example 1 the mass fraction ratios of Ca and Mg were determined in main histological compartments of the prostate tissue: glandular epithelium, stroma and lumen. The correlation coefficients (r-value) between the mass fraction of the element in a prostate tissue compartment and the relative volume of the main histological compartments of prostate tissue are given in the Table 4. For Ca and Mg a strong correlation with lumen was found indicating that the content of given markers is reflected in the prostatic fluid, which is the main part of the content of the prostate tissue lumen. Prostatic fluid is the part of the ejaculate and is present in urine too; therefore the concentration of the specific biomarkers will also be reflected in ejaculate and urine. As a result, prostate condition can be established using the biomarkers given in the Table 1 using prostatic fluid, seminal fluid and urine samples.

TABLE 4

Correlation coefficient (r-value) between the mass fraction of Ca and Mg in prostate tissue and the relative volume of the main histological compartments of prostate tissue.

| Compartment | Element | |
| --- | --- | --- |
| | Ca | Mg |
| Glandular epithelium | 0.194 | 0.385 |
| Stroma | −0.421 | −0.482 |
| Lumen | 0.582 | 0.437 |

Statistically significant r-values are given in bold

Example 17

Identification of Cancer Biomarkers in Expressed Prostatic Secretion Using Inductively Coupled Plasma Mass Spectrometry (ICP-MS) and Inductively Coupled Atomic Emission Spectrometry (ICP-AES)

Experimental conditions of the present study were approximated to the hospital conditions as closely as possible.

Equipment:
Inductively coupled plasma mass spectrometry instrument Agilent 7500c.

Specimen:
Expressed Prostatic Secretion samples (EPS) from patients with Benign Prostate Hyperplasia (BPH) and prostate adenocarcinoma (PCa) and EPS samples from healthy volunteers were obtained by transrectal prostate massage. The presence of cancer was confirmed by Digital Rectal Examination (DRE), TransRectal Ultrasound Imaging (TRUSI) and microscopic analysis of tissue morphology in biopsies obtained from the same patients. The absence of cancer was confirmed by DRE and TRUSI.

Reagents:
$HNO_3$ (nitric acid 65% for analysis, max. 0.005 ppm Hg, GR, ISO, Merck), $H_2O_2$ (hydrogen peroxide pure for analysis, Merck), ICP-MS standards NCSZC73013 (NCS Certified Reference Material), BCR063R (Community Bureau of Reference of the European Comission) and IRM-BD151 (LGC Standards, Weisel, Germany).

Protocol:
0.5 mL of $HNO_3$ was added to freeze-dried EPS samples and the samples were left over night at room temperature. After that 0.25 mL of $HNO_3$ and 0.15 mL of $H_2O_2$ were added to the samples and placed in water bath at 95° C. for 30 min. The heat-treated samples were cooled down to the room temperature; the soluble fraction was diluted with deionized water to 15 mL and transferred to a plastic measuring bottle. Simultaneously, the same procedure was performed on a sample containing no EPS fluid, and the resultant solution was used as a blank sample. All samples were analysed by Inductively Coupled Plasma Mass Spectrometry and Inductively Coupled Plasma Atomic Emission Spectrometry.

The spectrometer parameters and the main parameters of ICP-MS measurements: auxiliary air flow rate—0.9/min, nebulizer flow rate—0.9/min, sample update—0.8 mL/min. The spectrometer parameters for ICP-AES measurements: generator output power 1.500 W.

Results:
The content of Ag, Al, Au, B, Bi, Br, Cd, Ce, Co, Cr, Cs, Dy, Er, Gd, Hg, Ho, La, Li, Mn, Nd, Ni, Pb, Pr, Rb, S, Sb, Sc, Se, Si, Sm, Tb, Th, Tl, U, Y, and Zr in EPS was analysed by ICP-MS. The content of Na, Mg, P, S, K, Ca, Fe, Cu, Zn, Sr, and Ba in EPS was analysed by ICP-AES.

Statistically significant differences in mass fraction levels of 46 chemical elements (Table 5) were found in samples derived from cancerous, benign hyperplastic and normal prostate EPS. Differences in mass fraction levels of these elements can be used for diagnosis and therapeutic purpose. The data in Table 5 allow evaluating the importance of the individual chemical element content information for the diagnosis of prostate cancer (PCa).

TABLE 5

Comparison of mean values of chemical element mass fractions (mg · kg⁻¹, dry mass basis) in normal, benign hyperplastic (BPH) and cancerous (PCa) EPS.

| Element | Prostatic fluid Normal | Prostatic fluid BPH | Prostatic fluid PCa | Ratios of means BPH to Normal | Ratios of means PCa to Normal | Ratios of means PCa to BPH |
|---|---|---|---|---|---|---|
| Li | 0.45 | 0.18 | 0.21 | 0.4 | 0.5 | 1.2 |
| B | 0.97 | 2.54 | 1.00 | 2.6 | 1.0 | 0.4 |
| Na | 45440 | 47804 | 167000 | 1.1 | 3.7 | 3.5 |
| Mg | 5130 | 4549 | 1900 | 0.9 | 0.4 | 0.4 |
| Al | 4.63 | 12.50 | 43.85 | 2.7 | 9.5 | 3.5 |
| Si | 25.80 | 44.33 | 110.00 | 1.7 | 4.3 | 2.5 |
| P | 1732 | 4844 | 1800 | 2.8 | 1.0 | 0.4 |
| S | 5469 | 5063 | 6300 | 0.9 | 1.2 | 1.2 |
| K | 37920 | 27525 | 19000 | 0.7 | 0.5 | 0.7 |
| Ca | 11040 | 10758 | 3800 | 1.0 | 0.3 | 0.4 |
| Sc | 0.06 | 0.05 | 0.01 | 1.0 | 0.2 | 0.2 |
| Cr | 0.61 | 0.90 | 23.74 | 1.5 | 39.1 | 26.4 |
| Mn | 1.10 | 0.71 | 3.95 | 0.7 | 3.9 | 5.6 |
| Fe | 15.7 | 26.4 | 370.0 | 1.7 | 23.6 | 14.0 |
| Co | 0.03 | 0.05 | 0.08 | 1.3 | 2.5 | 1.9 |
| Ni | 0.32 | 4.58 | 7.03 | 14.2 | 21.9 | 1.5 |
| Cu | 8.46 | 13.65 | 14.45 | 1.6 | 1.7 | 1.1 |
| Zn | 8606 | 5099 | 2000 | 0.6 | 0.2 | 0.4 |
| Se | 1.56 | 1.45 | 0.10 | 0.9 | 0.1 | 0.1 |
| Br | 31.8 | 43.5 | 559.6 | 1.4 | 17.6 | 12.9 |
| Rb | 52.8 | 32.3 | 23.9 | 0.6 | 0.5 | 0.7 |
| Sr | 2.71 | 2.57 | 3.15 | 0.9 | 1.2 | 1.2 |
| Y | 0.01 | 0.01 | 0.03 | 1.3 | 2.6 | 2.0 |
| Zr | 0.07 | 0.14 | 0.47 | 2.1 | 6.8 | 3.3 |
| Ag | 0.03 | 0.37 | 0.94 | 14.4 | 36.2 | 2.5 |
| Sb | 0.10 | 0.51 | 0.10 | 5.1 | 1.0 | 0.2 |
| Cs | 0.08 | 0.08 | 0.10 | 1.1 | 1.3 | 1.2 |
| Ba | 0.35 | 0.35 | 3.31 | 1.0 | 9.4 | 9.4 |
| La | 0.06 | 0.02 | 0.04 | 0.4 | 0.8 | 2.3 |
| Ce | 0.01 | 0.02 | 0.08 | 1.2 | 6.2 | 5.1 |
| Pr | 0.06 | 0.01 | 0.02 | 0.2 | 0.4 | 2.0 |
| Nd | 0.01 | 0.03 | 0.04 | 2.5 | 3.7 | 1.5 |
| Sm | 0.01 | 0.01 | 0.02 | 1.1 | 2.4 | 2.3 |
| Gd | 0.01 | 0.01 | 0.04 | 1.2 | 3.6 | 3.0 |
| Tb | 0.01 | 0.01 | 0.01 | 1.0 | 1.4 | 1.4 |
| Dy | 0.01 | 0.01 | 0.02 | 1.0 | 1.9 | 1.9 |
| Ho | 0.01 | 0.01 | 0.01 | 1.0 | 1.2 | 1.2 |
| Er | 0.01 | 0.01 | 0.03 | 1.0 | 2.5 | 2.5 |
| Au | 0.07 | 0.19 | 0.01 | 2.6 | 0.1 | 0.1 |
| Cd | 0.03 | 0.08 | 0.37 | 3.3 | 14.4 | 4.3 |
| Hg | 0.08 | 0.05 | 0.0001 | 0.7 | 0.001 | 0.001 |
| Tl | 0.01 | 0.01 | 0.15 | 0.9 | 13.8 | 15.3 |
| Pb | 0.08 | 0.32 | 1.03 | 3.7 | 12.2 | 3.3 |
| Bi | 0.02 | 0.01 | 0.40 | 0.6 | 24.5 | 39.5 |
| Th | 0.03 | 0.01 | 0.04 | 0.5 | 1.7 | 3.8 |
| U | 0.01 | 0.01 | 0.05 | 1.0 | 4.8 | 4.8 |

Example 18

Identification of Cancer Biomarkers in Seminal Fluid Using Inductively Coupled Plasma Mass Spectrometry (ICP-MS) and Inductively Coupled Atomic Emission Spectrometry (ICP-AES)

Experimental conditions of the present study were approximated to the hospital conditions as closely as possible.

Equipment:

Inductively coupled plasma mass spectrometry instrument Agilent 7500c.

Specimen:

Ejaculate samples from patients with Benign Prostatic Hyperplasia, prostate adenocarcinoma and from healthy volunteers were obtained by masturbation into a clean metal-free vial. The presence of cancer was confirmed by DRE, TRUSI and microscopic analysis of tissue morphology in biopsies obtained from the same patients. The absence of cancer was confirmed by DRE and TRUSI.

Reagents:

$HNO_3$ (nitric acid 65% for analysis, max. 0.005 ppm Hg, GR, ISO, Merck), $H_2O_2$ (hydrogen peroxide pure for analysis, Merck), ICP-MS standards NCSZC73013 (NCS Certified Reference Material), BCR063R (Community Bureau of Reference of the European Comission) and IRM-BD151 (LGC Standards, Weisel, Germany).

Protocol:

0.5 mL of $HNO_3$ was added to freeze-dried seminal fluid samples and the samples were left over night at room temperature. After that 0.25 mL of $HNO_3$ and 0.15 mL of $H_2O_2$ were added to the samples and placed in water bath at 95° C. for 30 min. The heat-treated sample was cooled down to the room temperature; the soluble fraction was diluted with deionized water to 15 mL and transferred to a plastic measuring bottle. Simultaneously, the same procedure was performed on a sample containing no seminal fluid, and the resultant solution was used as a blank sample. All samples were analysed by Inductively Coupled Plasma Mass Spectrometry and Inductively Coupled Plasma Atomic Emission Spectrometry.

The spectrometer parameters and the main parameters of ICP-MS measurements: auxiliary air flow rate—0.9 L/min, nebulizer flow rate—0.9 L/min, sample update—0.8 mL/min. The spectrometer parameters for ICP-AES measurements: generator output power 1,500 W.

Results:

The content of Ag, Al, Au, B, Bi, Br, Cd, Ce, Co, Cr, Cs, Dy, Er, Gd, Hg, Ho, La, Li, Mn, Nd, Ni, Pb, Pr, Rb, S, Sb, Sc, Se, Si, Sm, Tb, Th, Tl, U, Y, and Zr in seminal fluid was analysed by ICP-MS. The content of Na, Mg, P, S. K, Ca, Fe, Cu, Zn, Sr, and Be in seminal fluid was analysed by ICP-AES.

Statistically significant differences in mass fraction levels of 46 chemical elements (Table 6) were found in seminal fluid samples derived from cancerous, benign hyperplastic and normal subjects. Differences in mass fraction levels of these elements can be used for diagnosis and therapeutic purpose. The data in Table 6 allow evaluating the importance of the individual chemical element content information for the diagnosis of prostate cancer (PCa).

TABLE 6

Comparison of mean values of chemical element mass fractions (mg · kg⁻¹, dry mass basis) in normal, benign hyperplastic (BPH) and cancerous (PCa) seminal fluid.

| Element | Seminal fluid Normal | Seminal fluid BPH | Seminal fluid PCa | Ratios of means BPH to Normal | Ratios of means PCa to Normal | Ratios of means PCa to BPH |
|---|---|---|---|---|---|---|
| Li | 0.04 | 0.17 | 0.01 | 4.6 | 0.32 | 0.1 |
| B | 0.80 | 4.19 | 1.00 | 5.2 | 1.25 | 0.2 |
| Na | 21489 | 42638 | 35000 | 2.0 | 1.63 | 0.8 |
| Mg | 1100 | 3674 | 140 | 8.2 | 0.13 | 0.04 |
| Al | 3.82 | 6.06 | 4.69 | 1.6 | 1.23 | 0.8 |
| Si | 6.31 | 29.35 | 11.92 | 4.6 | 1.89 | 0.4 |
| P | 10352 | 8453 | 15000 | 0.8 | 1.45 | 1.8 |
| S | 1966 | 4716 | 2700 | 2.4 | 1.37 | 0.6 |
| K | 5201 | 21428 | 3800 | 4.1 | 0.73 | 0.2 |
| Ca | 3034 | 8237 | 1300 | 5.0 | 0.43 | 0.2 |
| Sc | 0.05 | 0.04 | 0.01 | 0.9 | 0.22 | 0.2 |
| Cr | 0.41 | 0.55 | 1.20 | 1.3 | 2.91 | 2.2 |
| Mn | 0.23 | 0.35 | 0.12 | 1.6 | 0.55 | 0.4 |
| Fe | 19.0 | 17.3 | 8.5 | 0.9 | 0.45 | 0.5 |

TABLE 6-continued

Comparison of mean values of chemical element mass fractions (mg · kg⁻¹, dry mass basis) in normal, benign hyperplastic (BPH) and cancerous (PCa) seminal fluid.

| | Seminal fluid | | | Ratios of means | | |
|---|---|---|---|---|---|---|
| Element | Normal | BPH | PCa | BPH to Normal | PCa to Normal | PCa to BPH |
| Co | 0.01 | 0.03 | 0.01 | 2.9 | 1.00 | 0.3 |
| Ni | 0.22 | 3.27 | 0.10 | 14.6 | 0.45 | 0.03 |
| Cu | 2.16 | 12.67 | 0.99 | 5.9 | 0.46 | 0.1 |
| Zn | 731 | 4003 | 140 | 5.5 | 0.19 | 0.03 |
| Se | 0.68 | 1.41 | 0.36 | 2.1 | 0.54 | 0.3 |
| Br | 30.8 | 42.5 | 54.7 | 1.4 | 1.78 | 1.3 |
| Rb | 7.0 | 24.1 | 5.0 | 3.4 | 0.71 | 0.2 |
| Sr | 0.45 | 2.28 | 0.50 | 5.0 | 1.09 | 0.2 |
| Y | 0.01 | 0.01 | 0.01 | 0.7 | 0.73 | 1.0 |
| Zr | 0.08 | 0.08 | 0.05 | 1.0 | 0.59 | 0.6 |
| Ag | 0.01 | 0.01 | 0.03 | 1.0 | 2.99 | 3.0 |
| Sb | 0.10 | 0.10 | 0.01 | 1.0 | 0.10 | 0.1 |
| Cs | 0.01 | 0.06 | 0.01 | 4.5 | 0.99 | 0.2 |
| Ba | 0.13 | 0.25 | 0.13 | 1.9 | 1.01 | 0.5 |
| La | 0.10 | 0.01 | 0.01 | 0.1 | 0.10 | 1.0 |
| Ce | 0.01 | 0.01 | 0.01 | 1.0 | 0.81 | 0.8 |
| Pr | 0.01 | 0.01 | 0.01 | 1.0 | 1.00 | 1.0 |
| Nd | 0.01 | 0.01 | 0.01 | 1.0 | 1.00 | 1.0 |
| Sm | 0.01 | 0.01 | 0.00 | 1.0 | 0.16 | 0.2 |
| Gd | 0.01 | 0.01 | 0.01 | 1.0 | 1.00 | 1.0 |
| Tb | 0.01 | 0.01 | 0.01 | 1.0 | 1.00 | 1.0 |
| Dy | 0.01 | 0.01 | 0.01 | 1.0 | 1.00 | 1.0 |
| Ho | 0.01 | 0.01 | 0.01 | 1.0 | 1.00 | 1.0 |
| Er | 0.01 | 0.01 | 0.01 | 1.0 | 1.00 | 1.0 |
| Au | 0.02 | 0.07 | 0.01 | 3.1 | 0.44 | 0.1 |
| Cd | 0.01 | 0.03 | 0.02 | 2.1 | 1.58 | 0.7 |
| Hg | 0.04 | 0.05 | 0.01 | 1.4 | 0.01 | 0.2 |
| Tl | 0.01 | 0.01 | 0.01 | 1.0 | 1.00 | 1.0 |
| Pb | 0.10 | 0.14 | 0.08 | 1.4 | 0.85 | 0.6 |
| Bi | 0.01 | 0.01 | 0.02 | 0.8 | 1.27 | 1.7 |
| Th | 0.02 | 0.01 | 0.01 | 0.6 | 0.56 | 1.0 |
| U | 0.01 | 0.01 | 0.01 | 1.0 | 1.00 | 1.0 |

Example 19

Establishing the Prostate Condition Using Mn Mass Fraction in an EPS Sample

The tissue content of Mn was found to be significantly different in most cancerous EPS samples as compared to normal and benign hyperplastic EPS samples (Example 17, Table 5). Mass fraction of Mn in EPS of normal prostate was found to be 0.51 mg/kg, in BPH 1.10 mg/kg, and in PCa 3.95 mg/kg on dry mass basis (Table 5). The upper limit for Mn mass fraction in dry EPS from normal or BPH subject was determined to be M+2SD or 2.4 mg/kg on dry mass basis.

If PCa EPS needs to be discriminated from normal and BPH and if Mn content in the EPS sample prepared and analysed as described in the Example 17 exceeds 2.4 mg/kg dry EPS, prostate carcinoma can be diagnosed with an accuracy of 94±3%.

Example 20

Establishing the Prostate Condition Using Al Mass Fraction in an EPS Sample

The tissue content of Al was found to be significantly different in most cancerous EPS samples as compared to normal and benign hyperplastic EPS samples (Example 17, Table 5). Mass fraction of Al in EPS of normal prostate was found to be 4.63 mg/kg, in BPH 12.5 mg/kg, and in PCa 43.85 mg/kg on dry mass basis (Table 5). The upper limit for Al mass fraction in dry EPS from normal or BPH subject was determined to be M+2SD or 25 mg/kg on dry mass basis.

If EPS PCa needs to be discriminated from normal and BPH and if Al content in a EPS sample prepared and analysed as described in the Example 17 exceeds 25 mg/kg in dry EPS, carcinoma with an accuracy of 96±4% can be diagnosed.

Example 21

Establishing the Prostate Condition Using Ba Mass Fraction in an EPS Sample

The tissue content of Ba was found to be significantly different in most cancerous prostatic fluid samples as compared to normal and benign hyperplastic prostatic fluid samples (Example 17, Table 5). Mass fraction of Ba in EPS of normal prostate was found to be 0.35 mg/kg, in BPH 0.35 mg/kg, and in PCa 3.57 mg/kg on dry mass basis (Table 5). The upper limit for Ba mass fraction in dry EPS from normal or BPH subject was determined to be M+2SD or 1.5 mg/kg on dry mass basis.

If EPS PCa needs to be discriminated from normal and BPH and if Ba content in the EPS sample prepared and analysed as described in the Example 17 exceeds 2.5 mg/kg dry EPS, prostate carcinoma with an accuracy of 95±5% can be diagnosed.

Example 22

Establishing the Prostate Condition Using Bi Mass Fraction in an EPS Sample

The tissue content of Bi was found to be significantly different in most cancerous prostatic fluid samples as compared to normal and benign hyperplastic prostatic fluid samples (Example 17, Table 5). Mass fraction of Bi in EPS of normal prostate was found to be 0.02 mg/kg, in BPH 0.01 mg/kg, and in PCa 0.40 mg/kg on dry mass basis (Table 5). The upper limit for Bi mass fraction in dry EPS from normal or BPH subject was determined to be 0.04 mg/kg on dry mass basis.

If EPS PCa needs to be discriminated from normal and BPH and if Bi content in a seminal fluid sample prepared and analysed as described in the Example 17 exceeds 0.03 mg/kg dry EPS, prostate carcinoma with an accuracy of 96±3% can be diagnosed.

Example 23

Establishing the Prostate Condition Using Ca Mass Fraction in an EPS Sample

The tissue content of Ba was found to be significantly different in most cancerous prostatic fluid samples as compared to normal and benign hyperplastic prostatic fluid samples (Example 17, Table 5). Mass fraction of Ca in EPS of normal prostate was found to be 11040 mg/kg, in BPH 10758 mg/kg, and in PCa 3800 mg/kg on dry mass basis (Table 5). The lower limit for Ca mass fraction in dry EPS from normal or BPH subject was determined to be 8000 mg/kg on dry mass basis.

If EPS PCa needs to be discriminated from normal and BPH and if Ca content in the EPS sample prepared and analyzed as described in the Example 17 does not exceed 2000 mg/kg dry EPS, prostate carcinoma with an accuracy of 95±5% can be diagnosed.

Example 24

Establishing the Prostate Condition Using Mg Mass Fraction in an EPS Sample

The tissue content of Mg was found to be significantly different in most cancerous prostatic fluid samples as compared to normal and benign hyperplastic prostatic fluid samples (Example 17, Table 5). Mass fraction of Mg in EPS of normal prostate was found to be 5130 mg/kg, in BPH 4549 mg/kg, and in PCa 1900 mg/kg on dry mass basis (Table 5). The lower limit for Mg mass fraction in dry EPS from normal or BPH subject was determined to be 3500 mg/kg on dry mass basis.

If EPS PCa needs to be discriminated from normal and BPH and if mg content in the EPS sample prepared and analysed as described in the Example 17 does not exceed 3500 mg/kg dry EPS, prostate carcinoma with an accuracy of 95±5% can be diagnosed.

Example 25

Establishing the Prostate Condition Using Cr Mass Fraction in a Seminal Fluid Sample The tissue content of Cr was found to be significantly different in most cancerous seminal fluid samples as compared to normal and benign hyperplastic seminal fluid samples (Example 18, Table 6). Mass fraction of Cr in seminal fluid of normal prostate was found to be 0.41 mg/kg, in BPH 0.55 mg/kg, and in PCa 1.2 mg/kg on dry mass basis (Table 6). The upper limit for Cr mass fraction in dry seminal fluid from normal or BPH subject was determined to be 0.90 mg/kg on dry mass basis.

If PCa needs to be discriminated from normal and BPH and if Cr content in a seminal fluid sample prepared and analysed as described in the Example 18 exceeds 0.90 mg/kg dry tissue, prostate carcinoma with an accuracy of 94±3% can be diagnosed.

Example 26

Establishing the Prostate Condition Using Mg Mass Fraction in a Seminal Fluid Sample The tissue content of Mg was found to be significantly different in most cancerous seminal fluid samples as compared to normal and benign hyperplastic seminal fluid samples (Example 18, Table 6). Mass fraction of Mg in seminal fluid of normal prostate was found to be 1100 mg/kg, in BPH 3674 mg/kg, and in PCa 140 mg/kg on dry mass basis (Table 6). The lower limit for Mg mass fraction in seminal fluid from normal or BPH subject was determined to be 700 mg/kg on dry mass basis.

If PCa needs to be discriminated from normal and BPH and if Mg content in a seminal fluid sample prepared and analysed as described in the Example 18 does not exceed 700 mg/kg dry tissue, prostate carcinoma with an accuracy of 92±5% can be diagnosed.

Example 26

Establishing the Prostate Condition Using Ca Mass Fraction in a Seminal Fluid Sample The tissue content of Ca was found to be significantly different in most cancerous seminal fluid samples as compared to normal and benign hyperplastic seminal fluid samples (Example 18, Table 6). Mass fraction of Ca in seminal fluid of normal prostate was found to be 3030 mg/kg, in BPH 8237 mg/kg, and in PCa 1300 mg/kg on dry mass basis (Table 6). The lower limit for Ca mass fraction in dry seminal fluid from normal or BPH subject was determined to 2200 mg/kg on dry mass basis.

If PCa needs to be discriminated from normal and BPH and if Ca content in a seminal fluid sample prepared and analysed as described in the Example 18 does not exceed 2200 mg/kg dry tissue, prostate carcinoma with an accuracy of 90±5% can be diagnosed.

Example 27

Determination of Mass Fraction Levels of 44 Elements Relative to the Mass Fraction of Calcium in Normal, Cancerous and BPH EPS Mass fraction ratios of the elements mentioned in the Example 17 are different in non-cancerous and cancerous EPS and therefore these can be used as prostate tumor biomarkers. In the Table 7 mass fraction ratios of 44 elements relative to mass fraction of calcium are presented. Further, ratios of the mass fraction ratios for EPS from normal, BPH and cancerous subjects are given. The data in the Table 7 allow evaluating the importance of individual mass fraction ratios of 44 elements relative to the mass fraction of calcium for the diagnosis of PCa.

TABLE 7

Means of ratios and their ratios between mean values of mass fraction ratios of Ca to mass fractions of other chemical elements in EPS from normal, benign hyperplastic (BPH) and cancerous (PCa) subjects.

| | Prostatic fluid | | | Ratios of means | | |
|---|---|---|---|---|---|---|
| Element | Normal | BPH | PCa | BPH to Normal | PCa to Normal | PCa to BPH |
| Ca/Li | 24530 | 60481 | 18046 | 2.5 | 0.7 | 0.3 |
| Ca/B | 11328 | 4233 | 3800 | 0.4 | 0.3 | 0.9 |
| Ca/Na | 0.2 | 0.2 | 0.0 | 0.9 | 0.1 | 0.1 |
| Ca/Mg | 2.2 | 2.4 | 2.0 | 1.1 | 0.9 | 0.8 |
| Ca/Al | 2386 | 861 | 87 | 0.4 | 0.04 | 0.1 |
| Ca/Si | 428 | 243 | 35 | 0.6 | 0.1 | 0.1 |
| Ca/P | 6.4 | 2.2 | 2.1 | 0.3 | 0.3 | 1.0 |
| Ca/S | 2.0 | 2.1 | 0.6 | 1.1 | 0.3 | 0.3 |
| Ca/K | 0.3 | 0.4 | 0.2 | 1.3 | 0.7 | 0.5 |
| Ca/Sc | 192704 | 195808 | 380000 | 1.0 | 2.0 | 1.9 |
| Ca/Cr | 18189 | 11976 | 160 | 0.7 | 0.01 | 0.01 |
| Ca/Mn | 10931 | 15155 | 962 | 1.4 | 0.09 | 0.1 |
| Ca/Fe | 703 | 407 | 10 | 0.6 | 0.01 | 0.03 |
| Ca/Co | 327111 | 236917 | 44829 | 0.7 | 0.1 | 0.2 |
| Ca/Ni | 34350 | 2350 | 541 | 0.1 | 0.02 | 0.2 |
| Ca/Cu | 1304 | 788 | 263 | 0.6 | 0.2 | 0.3 |
| Ca/Zn | 1.3 | 2.1 | 1.9 | 1.6 | 1.5 | 0.9 |
| Ca/Se | 7072 | 7429 | 38000 | 1.1 | 5.4 | 5.1 |
| Ca/Br | 347 | 247 | 7 | 0.7 | 0.02 | 0.03 |
| Ca/Rb | 209 | 333 | 159 | 1.6 | 0.8 | 0.5 |
| Ca/Sr | 4074 | 4179 | 1206 | 1.0 | 0.3 | 0.3 |
| Ca/Y | 1062560 | 769711 | 138346 | 0.7 | 0.1 | 0.2 |

TABLE 7-continued

Means of ratios and their ratios between mean values of mass fraction ratios of Ca to mass fractions of other chemical elements in EPS from normal, benign hyperplastic (BPH) and cancerous (PCa) subjects.

| | Prostatic fluid | | | Ratios of means | | |
|---|---|---|---|---|---|---|
| Element | Normal | BPH | PCa | BPH to Normal | PCa to Normal | PCa to BPH |
| Ca/Zr | 160360 | 75539 | 8171 | 0.5 | 0.1 | 0.1 |
| Ca/Ag | 425598 | 28803 | 4046 | 0.1 | 0.01 | 0.1 |
| Ca/Sb | 110400 | 21303 | 38000 | 0.2 | 0.3 | 1.8 |
| Ca/Cs | 141702 | 126577 | 36370 | 0.9 | 0.3 | 0.3 |
| Ca/Ba | 31319 | 30715 | 1148 | 1.0 | 0.04 | 0.04 |
| Ca/La | 199512 | 549579 | 84542 | 2.8 | 0.4 | 0.2 |
| Ca/Ce | 859311 | 699707 | 48008 | 0.8 | 0.1 | 0.1 |
| Ca/Pr | 200727 | 1005734 | 174020 | 5.0 | 0.9 | 0.2 |
| Ca/Nd | 991023 | 389312 | 91545 | 0.4 | 0.1 | 0.2 |
| Ca/Sm | 1104000 | 1019233 | 156230 | 0.9 | 0.1 | 0.2 |
| Ca/Gd | 1104000 | 903780 | 106736 | 0.8 | 0.1 | 0.1 |
| Ca/Tb | 1104000 | 1075800 | 263046 | 1.0 | 0.2 | 0.2 |
| Ca/Dy | 1104000 | 1091721 | 198095 | 1.0 | 0.2 | 0.2 |
| Ca/Ho | 1104000 | 1075800 | 315152 | 1.0 | 0.3 | 0.3 |
| Ca/Er | 1104000 | 1075800 | 151557 | 1.0 | 0.1 | 0.1 |
| Ca/Au | 154190 | 57363 | 380000 | 0.4 | 2.5 | 6.6 |
| Ca/Cd | 431048 | 126876 | 10313 | 0.3 | 0.02 | 0.1 |
| Ca/Hg | 143862 | 215160 | 76000000 | 1.5 | 528.3 | 353.2 |
| Ca/Tl | 995043 | 1075800 | 24762 | 1.1 | 0.02 | 0.02 |
| Ca/Pb | 130574 | 33968 | 3684 | 0.3 | 0.03 | 0.1 |
| Ca/Bi | 671533 | 1056778 | 9446 | 1.6 | 0.01 | 0.01 |
| Ca/Th | 431082 | 926283 | 86428 | 2.1 | 0.2 | 0.1 |
| Ca/U | 1104000 | 1075800 | 79838 | 1.0 | 0.1 | 0.1 |

Example 27

Determination of Mass Fraction Levels of 44 Elements Relative to the Mass Fraction of Zinc in Normal, Cancerous and BPH EPS Mass fraction ratios of the elements mentioned in the Example 17 are different in non-cancerous and cancerous EPS and therefore these can be used as prostate tumor biomarkers. In the Table 8 mass fraction ratios of 44 elements relative to mass fraction of zinc are presented. Further, ratios of the mass fraction ratios for EPS from normal, BPH and cancerous subjects are given. The data in the Table 8 allow evaluating the importance of individual mass fraction ratios of 44 elements relative to the mass fraction of zinc for the diagnosis of PCa.

TABLE 8

Means of ratios and their ratios between mean values of mass fraction ratios of Zn to mass fractions of other chemical elements in EPS from normal, benign hyperplastic (BPH) and cancerous (PCa) subjects.

| Mass fraction ratio | Prostatic fluid | | | Ratios of means | | |
|---|---|---|---|---|---|---|
| | Normal | BPH | PCa | BPH to Normal | PCa to Normal | PCa to BPH |
| Zn/Li | 19121 | 28666 | 9498 | 1.50 | 0.50 | 0.33 |
| Zn/B | 8830 | 2006 | 2000 | 0.23 | 0.23 | 1.00 |
| Zn/Na | 0.2 | 0.1 | 0.0 | 0.56 | 0.06 | 0.11 |
| Zn/Mg | 1.7 | 1.1 | 1.1 | 0.67 | 0.63 | 0.94 |
| Zn/Al | 1860.0 | 407.9 | 45.6 | 0.22 | 0.02 | 0.11 |
| Zn/Si | 333.6 | 115.0 | 18.2 | 0.34 | 0.05 | 0.16 |
| Zn/P | 5.0 | 1.1 | 1.1 | 0.21 | 0.22 | 1.06 |
| Zn/S | 1.6 | 1.0 | 0.3 | 0.64 | 0.20 | 0.32 |
| Zn/K | 0.2 | 0.2 | 0.1 | 0.82 | 0.46 | 0.57 |
| Zn/Ca | 0.8 | 0.5 | 0.5 | 0.61 | 0.68 | 1.11 |
| Zn/Sc | 150218 | 92808 | 200000 | 0.62 | 1.33 | 2.15 |
| Zn/Cr | 14179 | 5676 | 84 | 0.40 | 0.01 | 0.01 |
| Zn/Mn | 8521 | 7183 | 506 | 0.84 | 0.06 | 0.07 |
| Zn/Fe | 548.2 | 193.0 | 5.4 | 0.35 | 0.01 | 0.03 |
| Zn/Co | 254993 | 112292 | 23594 | 0.44 | 0.09 | 0.21 |
| Zn/Ni | 26777 | 1114 | 285 | 0.04 | 0.01 | 0.26 |
| Zn/Cu | 1017 | 374 | 138 | 0.37 | 0.14 | 0.37 |
| Zn/Se | 5513 | 3521 | 20000 | 0.64 | 3.63 | 5.68 |
| Zn/Br | 270.3 | 117.2 | 3.6 | 0.43 | 0.01 | 0.03 |
| Zn/Rb | 162.9 | 157.7 | 83.8 | 0.97 | 0.51 | 0.53 |
| Zn/Sr | 3175 | 1981 | 635 | 0.62 | 0.20 | 0.32 |
| Zn/Y | 828296 | 364822 | 72814 | 0.44 | 0.09 | 0.20 |
| Zn/Zr | 125005 | 35803 | 4301 | 0.29 | 0.03 | 0.12 |
| Zn/Ag | 331766 | 13652 | 2129 | 0.04 | 0.01 | 0.16 |
| Zn/Sb | 86060 | 10097 | 20000 | 0.12 | 0.23 | 1.98 |
| Zn/Cs | 110461 | 59994 | 19142 | 0.54 | 0.17 | 0.32 |
| Zn/Ba | 24414 | 14558 | 604 | 0.60 | 0.02 | 0.04 |
| Zn/La | 155525 | 260485 | 44496 | 1.67 | 0.29 | 0.17 |
| Zn/Ce | 669858 | 331642 | 25267 | 0.50 | 0.04 | 0.08 |
| Zn/Pr | 156473 | 476691 | 91590 | 3.05 | 0.59 | 0.19 |
| Zn/Nd | 772531 | 184524 | 48182 | 0.24 | 0.06 | 0.26 |
| Zn/Sm | 860600 | 483089 | 82226 | 0.56 | 0.10 | 0.17 |
| Zn/Gd | 860600 | 428367 | 56177 | 0.50 | 0.07 | 0.13 |
| Zn/Tb | 860600 | 509900 | 138445 | 0.59 | 0.16 | 0.27 |
| Zn/Dy | 860600 | 517446 | 104261 | 0.60 | 0.12 | 0.20 |
| Zn/Ho | 860600 | 509900 | 165869 | 0.59 | 0.19 | 0.33 |
| Zn/Er | 860600 | 509900 | 79767 | 0.59 | 0.09 | 0.16 |
| Zn/Au | 120196 | 27189 | 200000 | 0.23 | 1.66 | 7.36 |
| Zn/Cd | 336014 | 60136 | 5428 | 0.18 | 0.02 | 0.09 |
| Zn/Hg | 112145 | 101980 | 40000000 | 0.91 | 356.68 | 392.23 |
| Zn/Tl | 775665 | 509900 | 13033 | 0.66 | 0.02 | 0.03 |
| Zn/Pb | 101786 | 16100 | 1939 | 0.16 | 0.02 | 0.12 |
| Zn/Bi | 523479 | 500884 | 4972 | 0.96 | 0.01 | 0.01 |
| Zn/Th | 336041 | 439033 | 45488 | 1.31 | 0.14 | 0.10 |
| Zn/U | 860600 | 509900 | 42020 | 0.59 | 0.05 | 0.08 |

Example 27

Determination of Mass Fraction Levels of 44 Elements Relative to the Mass Fraction of Calcium in Seminal Fluid from Normal, Cancerous and BPH Subjects Mass fraction ratios of the elements mentioned in the Example 18 are different in non-cancerous and cancerous seminal fluid and therefore these can be used as prostate tumor biomarkers. In the Table 9 mass fraction ratios of 44 elements relative to mass fraction of calcium are presented. Further, ratios of the mass fraction ratios for seminal fluid from normal, BPH and cancerous subjects are given. The data in the Table 9 allow evaluating the importance of individual mass fraction ratios of 44 elements relative to the mass fraction of calcium for the diagnosis of PCa.

TABLE 9

Means of ratios and their ratios between mean values of mass fraction ratios of Ca to mass fractions of other chemical elements in seminal fluid derived from normal, benign hyperplastic (BPH) and cancerous (PCa) subjects.

| Mass fraction ratio | Seminal fluid | | | Ratios of means | | |
|---|---|---|---|---|---|---|
| | Normal | BPH | PCa | BPH to Normal | PCa to Normal | PCa to BPH |
| Ca/Li | 82584 | 48711 | 109809 | 0.6 | 1.3 | 2.3 |
| Ca/B | 3801 | 1967 | 1300 | 0.5 | 0.3 | 0.7 |
| Ca/Na | 0.1 | 0.2 | 0.04 | 1.4 | 0.3 | 0.2 |
| Ca/Mg | 2.8 | 2.2 | 9.3 | 0.8 | 3.4 | 4.1 |
| Ca/Al | 794 | 1360 | 277 | 1.7 | 0.3 | 0.2 |
| Ca/Si | 481 | 281 | 109 | 0.6 | 0.2 | 0.4 |
| Ca/P | 0.3 | 1.0 | 0.1 | 3.3 | 0.3 | 0.1 |
| Ca/S | 1.5 | 1.7 | 0.5 | 1.1 | 0.3 | 0.3 |
| Ca/K | 0.6 | 0.4 | 0.3 | 0.7 | 0.6 | 0.9 |
| Ca/Sc | 65758 | 196333 | 130000 | 3.0 | 2.0 | 0.7 |
| Ca/Cr | 7331 | 15114 | 1079 | 2.1 | 0.1 | 0.1 |
| Ca/Mn | 13462 | 23277 | 10428 | 1.7 | 0.8 | 0.4 |
| Ca/Fe | 160 | 476 | 152 | 3.0 | 1.0 | 0.3 |
| Ca/Co | 303400 | 284857 | 130000 | 0.9 | 0.4 | 0.5 |
| Ca/Ni | 13565 | 2520 | 13050 | 0.2 | 1.0 | 5.2 |
| Ca/Cu | 1403 | 650 | 1316 | 0.5 | 0.9 | 2.0 |
| Ca/Zn | 4.2 | 2.1 | 9.3 | 0.5 | 2.2 | 4.5 |
| Ca/Se | 4480 | 5858 | 3567 | 1.3 | 0.8 | 0.6 |
| Ca/Br | 99 | 194 | 24 | 2.0 | 0.2 | 0.1 |
| Ca/Rb | 431 | 342 | 260 | 0.8 | 0.6 | 0.8 |
| Ca/Sr | 6691 | 3614 | 2625 | 0.5 | 0.4 | 0.7 |
| Ca/Y | 221025 | 823700 | 130000 | 3.7 | 0.6 | 0.2 |
| Ca/Zr | 39388 | 109571 | 28524 | 2.8 | 0.7 | 0.3 |
| Ca/Ag | 303400 | 823700 | 43458 | 2.7 | 0.1 | 0.1 |
| Ca/Sb | 30340 | 82370 | 130000 | 2.7 | 4.1 | 1.6 |
| Ca/Cs | 219853 | 131731 | 95502 | 0.6 | 0.4 | 0.7 |
| Ca/Ba | 22721 | 32499 | 9663 | 1.4 | 0.4 | 0.3 |
| Ca/La | 30340 | 830622 | 130000 | 27.4 | 4.3 | 0.2 |
| Ca/Ce | 267497 | 739297 | 140752 | 2.8 | 0.5 | 0.2 |
| Ca/Pr | 303400 | 823700 | 130000 | 2.7 | 0.4 | 0.2 |
| Ca/Nd | 303400 | 823700 | 130000 | 2.7 | 0.4 | 0.2 |
| Ca/Sm | 303400 | 823700 | 830635 | 2.7 | 2.7 | 1.0 |
| Ca/Gd | 303400 | 823700 | 130000 | 2.7 | 0.4 | 0.2 |
| Ca/Tb | 303400 | 823700 | 130000 | 2.7 | 0.4 | 0.2 |
| Ca/Dy | 303400 | 823700 | 130000 | 2.7 | 0.4 | 0.2 |
| Ca/Ho | 303400 | 823700 | 130000 | 2.7 | 0.4 | 0.2 |
| Ca/Er | 303400 | 823700 | 130000 | 2.7 | 0.4 | 0.2 |
| Ca/Au | 134556 | 116232 | 130000 | 0.9 | 1.0 | 1.1 |
| Ca/Cd | 252833 | 324298 | 68768 | 1.3 | 0.3 | 0.2 |
| Ca/Hg | 84303 | 164740 | 130000 | 2.0 | 1.5 | 0.8 |
| Ca/Tl | 303400 | 823700 | 130000 | 2.7 | 0.4 | 0.2 |
| Ca/Pb | 30681 | 58599 | 15384 | 1.9 | 0.5 | 0.3 |
| Ca/Bi | 232725 | 823700 | 78432 | 3.5 | 0.3 | 0.1 |
| Ca/Th | 169944 | 823769 | 130000 | 4.8 | 0.8 | 0.2 |
| Ca/U | 303400 | 823700 | 130000 | 2.7 | 0.4 | 0.2 |

TABLE 10

Means of ratios and their ratios between mean values of mass fraction ratios of Zn to mass fractions of other chemical elements in seminal fluid derived from normal, benign hyperplastic (BPH) and cancerous (PCa) subjects.

| Mass fraction ratio | Seminal fluid | | | Ratios of means | | |
|---|---|---|---|---|---|---|
| | Normal | BPH | PCa | BPH to Normal | PCa to Normal | PCa to BPH |
| Zn/Li | 19898 | 23655 | 11826 | 1.19 | 0.59 | 0.50 |
| Zn/B | 916 | 955 | 140 | 1.04 | 0.15 | 0.15 |
| Zn/Na | 0.03 | 0.1 | 0.004 | 2.76 | 0.12 | 0.04 |
| Zn/Mg | 1.6 | 1.1 | 1.0 | 0.67 | 0.62 | 0.92 |
| Zn/Al | 191.3 | 660.2 | 29.8 | 3.45 | 0.16 | 0.05 |
| Zn/Si | 115.8 | 136.3 | 11.7 | 1.18 | 0.10 | 0.09 |
| Zn/P | 0.1 | 0.5 | 0.01 | 6.70 | 0.13 | 0.02 |
| Zn/S | 0.4 | 0.8 | 0.1 | 2.28 | 0.14 | 0.06 |
| Zn/K | 0.1 | 0.2 | 0.04 | 1.33 | 0.26 | 0.20 |
| Zn/Ca | 0.4 | 0.5 | 0.1 | 1.10 | 0.24 | 0.22 |
| Zn/Sc | 15844 | 95342 | 14000 | 6.02 | 0.88 | 0.15 |
| Zn/Cr | 1766 | 7339 | 116 | 4.16 | 0.07 | 0.02 |
| Zn/Mn | 3243 | 11303 | 1123 | 3.49 | 0.35 | 0.10 |
| Zn/Fe | 38.5 | 231.0 | 16.4 | 6.00 | 0.43 | 0.07 |
| Zn/Co | 73100 | 138331 | 14000 | 1.89 | 0.19 | 0.10 |
| Zn/Ni | 3268 | 1224 | 1405 | 0.37 | 0.43 | 1.15 |
| Zn/Cu | 338 | 316 | 142 | 0.93 | 0.42 | 0.45 |
| Zn/Se | 1079.4 | 2844.5 | 384.1 | 2.64 | 0.36 | 0.14 |
| Zn/Br | 23.8 | 94.1 | 2.6 | 3.96 | 0.11 | 0.03 |
| Zn/Rb | 103.9 | 166.2 | 28.0 | 1.60 | 0.27 | 0.17 |
| Zn/Sr | 1612 | 1755 | 283 | 1.09 | 0.18 | 0.16 |
| Zn/Y | 53253 | 400000 | 14000 | 7.51 | 0.26 | 0.04 |
| Zn/Zr | 9490 | 53209 | 3072 | 5.61 | 0.32 | 0.06 |
| Zn/Ag | 73100 | 400000 | 4680 | 5.47 | 0.06 | 0.01 |
| Zn/Sb | 7310 | 40000 | 14000 | 5.47 | 1.92 | 0.35 |
| Zn/Cs | 52970 | 63970 | 10285 | 1.21 | 0.19 | 0.16 |
| Zn/Ba | 5474 | 15782 | 1041 | 2.88 | 0.19 | 0.07 |
| Zn/La | 7310 | 403361 | 14000 | 55.18 | 1.92 | 0.03 |
| Zn/Ce | 64450 | 359013 | 15158 | 5.57 | 0.24 | 0.04 |
| Zn/Pr | 73100 | 400000 | 14000 | 5.47 | 0.19 | 0.04 |
| Zn/Nd | 73100 | 400000 | 14000 | 5.47 | 0.19 | 0.04 |
| Zn/Sm | 73100 | 400000 | 89453 | 5.47 | 1.22 | 0.22 |
| Zn/Gd | 73100 | 400000 | 14000 | 5.47 | 0.19 | 0.04 |
| Zn/Tb | 73100 | 400000 | 14000 | 5.47 | 0.19 | 0.04 |
| Zn/Dy | 73100 | 400000 | 14000 | 5.47 | 0.19 | 0.04 |
| Zn/Ho | 73100 | 400000 | 14000 | 5.47 | 0.19 | 0.04 |
| Zn/Er | 73100 | 400000 | 14000 | 5.47 | 0.19 | 0.04 |
| Zn/Au | 32419 | 56444 | 14000 | 1.74 | 0.43 | 0.25 |
| Zn/Cd | 60917 | 157532 | 7406 | 2.59 | 0.12 | 0.05 |
| Zn/Hg | 20312 | 80000 | 14000 | 3.94 | 0.69 | 0.18 |
| Zn/Tl | 73100 | 400000 | 14000 | 5.47 | 0.19 | 0.04 |
| Zn/Pb | 7392 | 28456 | 1657 | 3.85 | 0.22 | 0.06 |
| Zn/Bi | 56072 | 400000 | 8447 | 7.13 | 0.15 | 0.02 |
| Zn/Th | 40946 | 400033 | 14000 | 9.77 | 0.34 | 0.03 |
| Zn/U | 73100 | 400000 | 14000 | 5.47 | 0.19 | 0.04 |

Example 28

Determination of Mass Fraction Levels of 44 Elements Relative to the Mass Fraction of Zinc in Seminal Fluid Derived from Normal, Cancerous and BPH Subjects Mass fraction ratios of the elements mentioned in the Example 18 are different in non-cancerous and cancerous seminal fluid and therefore these can be used as prostate tumor biomarkers. In the Table 10 mass fraction ratios of 44 elements relative to mass fraction of zinc are presented. Further, ratios of the mass fraction ratios for normal seminal fluid, BPH and cancerous seminal fluid are given. The data in the Table 10 allow evaluating the importance of individual mass fraction ratios of 44 elements relative to the mass fraction of calcium for the diagnosis of PCa.

Example 29

Using the Ca/Mn Mass Fraction Ratio in EPS to Establish Prostate Condition

The Ca/Mn mass fraction ratio in EPS was found to be significantly different in most cancerous EPS as compared to normal and benign hyperplastic EPS. The upper limit for Ca/Mn mass fraction ratio on dry mass basis in cancerous EPS was determined to be 1900 (Table 7).

If PCa needs to be discriminated from normal and BPH and if the Ca/Mn ratio in the EPS sample prepared and analysed as described in Example 17 does not exceed 1900, prostate carcinoma with an accuracy exceeding 96% can be diagnosed.

Example 30

Using the Ca/Al Mass Fraction Ratio in Seminal Fluid to Establish Prostate Condition The Ca/Al mass fraction ratio in seminal fluid was found to be significantly different in most cancerous seminal fluid as compared to normal and benign hyperplastic seminal fluid. The upper limit for Ca/Al mass fraction ratio on dry mass basis in cancerous seminal fluid was determined to be 290 (Table 9).

If PCa seminal fluid needs to be discriminated from normal and BPH one and if the Ca/Al ratio in the seminal fluid sample prepared and analysed as described in Example 18 does not exceed 290, prostate carcinoma with an accuracy exceeding 98% can be diagnosed.

Example 31

Using the Zn/Cu Mass Fraction Ratio in EPS to Establish Prostate Condition

The Zn/Cu mass fraction ratio in EPS was found to be significantly different in most cancerous EPS as compared to normal and benign hyperplastic EPS. The upper limit for Zn/Cu mass fraction ratio on dry mass basis in cancerous EPS was determined to be 165 (Table 8).

If PCa EPS needs to be discriminated from normal and BPH EPS and if the Zn/Cu ratio in the EPS sample prepared and analysed as described in Example 17 does not exceed 165, prostate carcinoma with an accuracy of 95% can be diagnosed.

Example 32

Using the Zn/Cu Mass Fraction Ratio in Seminal Fluid to Establish Prostate Condition The Zn/Cu mass fraction ratio in seminal fluid was found to be significantly different in most cancerous seminal fluids as compared to normal and benign hyperplastic seminal fluid. The upper limit for Zn/Cu mass fraction ratio on dry mass basis in cancerous seminal fluid was determined to be 155 (Table 10).

If PCa EPS needs to be discriminated from normal and BPH EPS and if the Zn/Cu ratio in the EPS sample prepared and analysed as described in Example 18 does not exceed 155, prostate carcinoma with an accuracy better than 95% can be diagnosed.

Example 33

Using the Ca*Mg*Zn/Mn*Bi*Se Mass Fraction Ratio Combination in EPS to Establish Prostate Condition The Ca*Mg*Zn/Mn*Bi*Se mass fraction ratio in EPS was found to be significantly different in most cancerous EPS as compared to normal and benign hyperplastic EPS. The lower limit for Ca*Mg*Zn/Mn*Bi*Se mass fraction ratio on dry mass basis in healthy EPS was determined to be 2E8.

If PCa EPS needs to be discriminated from normal and BPH EPS and if the Ca*Mg*Zn/Mn*Bi*Se ratio in the EPS sample prepared and analysed as described in Example 18 is below 2E8, prostate carcinoma with an accuracy better than 95% can be diagnosed.

Example 34

Using the Ca*Mg*Zn/Mn*Bi*Se Mass Fraction Ratio Combination in Seminal Fluid to Establish Prostate Condition The Ca*Mg*Zn/Mn*Bi*Se mass fraction ratio in seminal fluid was found to be significantly different in most cancerous seminal fluids as compared to normal and benign hyperplastic seminal fluid. The lower limit for Ca*Mg*Zn/Mn*Bi*Se mass fraction ratio on dry mass basis in healthy seminal fluid was determined to be 2E6.

If PCa seminal fluid needs to be discriminated from normal and BPH seminal fluid and if the Ca*Mg*Zn/Mn*Bi*Se ratio in the seminal fluid sample prepared and analysed as described in Example 19 is below 2E6, prostate carcinoma with an accuracy better than 95% can be diagnosed.

Example 35

Using the Ca/Ba Mass Fraction Ratio to Establish Prostate Condition

Figure 13:
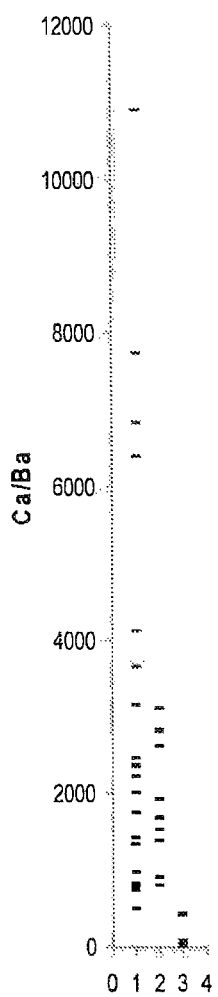
FIG. 13 shows individual data sets for Ca/Ba mass fraction ratio in samples of normal (1), benign hyperplastic (2) and cancerous prostate tissue (3).

The Ca/Ba mass fraction ratio was found to be significantly different in most cancerous prostate tissues as compared to normal and benign hyperplastic tissues (Example 8, Table 2). The upper limit for Ca/Ba mass fraction ratio on dry mass basis in cancerous prostate tissue was determined to be M+3SD (M—arithmetic mean, SD—standard deviation) or 400 (FIG. 13).

If PCa needs to be discriminated from normal and BPH tissue and if the Ca/Ba ratio in a prostate biopsy sample prepared and analysed as described in Example 1 does not exceed 400, prostate carcinoma with an accuracy of 100-2% can be diagnosed. The sensitivity and specificity of the Ca/Ba ratio based test is 100-9% and 100-2%, respectively.

Example 36

Using the Ca/P Mass Fraction Ratio to Establish Prostate Condition

Figure 14:
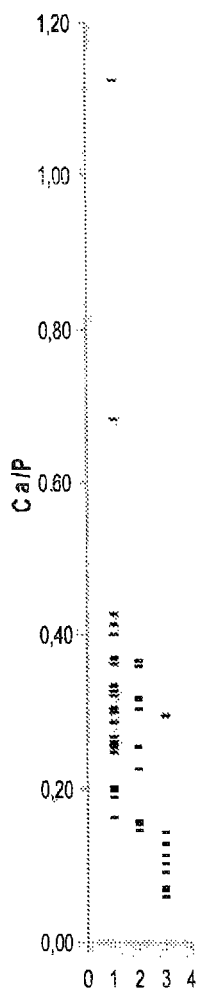
FIG. 14 shows individual data sets for Ca/P mass fraction ratio in samples of normal (1), benign hyperplastic (2) and cancerous prostate tissue (3).

The Ca/P mass fraction ratio was found to be significantly different in most cancerous prostate tissues as compared to normal and benign hyperplastic tissues (Example 8, Table 2). The upper limit for Ca/P mass fraction ratio on dry mass basis in cancerous prostate tissue was determined to be M+3SD (M—arithmetic mean, SD—standard deviation) or 0.15 (FIG. 14).

If PCa needs to be discriminated from normal and BPH tissue and if the Ca/P ratio in a prostate biopsy sample prepared and analysed as described in Example 1 does not exceed 0.15, prostate carcinoma with an accuracy of 98±2% can be diagnosed. The sensitivity and specificity of the Ca/P ratio based test is 91±9% and 100-3%, respectively.

Example 37

Using the Ca/Si Mass Fraction Ratio to Establish Prostate Condition

Figure 15:
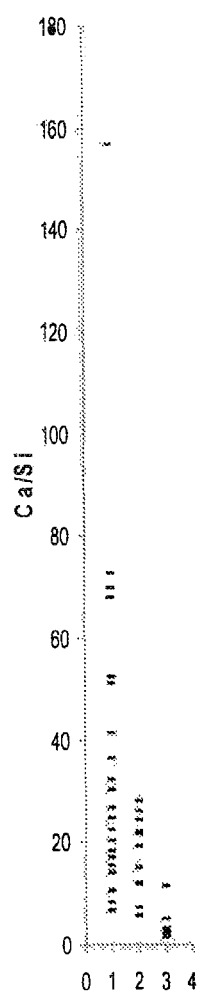
FIG. 15 shows individual data sets for Ca/Si mass fraction ratio in samples of normal (1), benign hyperplastic (2) and cancerous prostate tissue (3).
Figure 16:
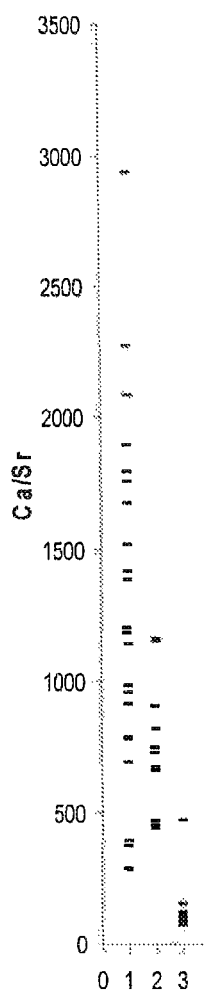
FIG. 16 shows individual data sets for Ca/Sr mass fraction ratio in samples of normal (1), benign hyperplastic (2) and cancerous prostate tissue (3).

The Ca/Si mass fraction ratio was found to be significantly different in most cancerous prostate tissues as compared to normal and benign hyperplastic tissues (Example 8, Table 2). The upper limit for Ca/Si mass fraction ratio on dry mass basis in cancerous prostate tissue was determined to be M+3SD (M—arithmetic mean, SD—standard deviation) or 5 (FIG. 15).

If PCa needs to be discriminated from normal and BPH tissue and if the Ca/Si ratio in a prostate biopsy sample prepared and analysed as described in Example 1 does not exceed 5, prostate carcinoma with an accuracy of 98±2% can be diagnosed. The sensitivity and specificity of the Ca/Si ratio based test is 91±9% and 100-3%, respectively.

Example 38

Using the Ca/Sr Mass Fraction Ratio to Establish Prostate Condition

Figure 18:
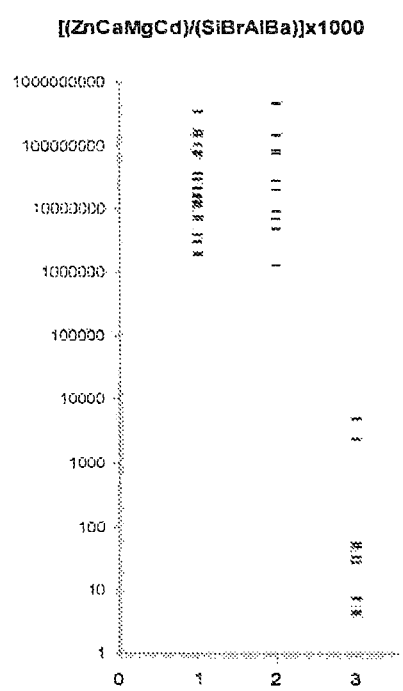
FIG. 18 shows individual data sets for [(Zn*Ca*Mg*Cd)/(Si*Br*Al*Ba)]*1000 mass fraction ratio in samples of normal (1), benign hyperplastic (2) and cancerous prostate tissue (3).

The Ca/Sr mass fraction ratio was found to be significantly different in most cancerous prostate tissues as compared to normal and benign hyperplastic tissues (Example 8, Table 2). The upper limit for Ca/Sr mass fraction ratio on dry mass basis in cancerous prostate tissue was determined to be M+3SD (M—arithmetic mean, SD—standard deviation) or 250 (FIG. 18).

If PCa needs to be discriminated from normal and BPH tissue and if the Ca/Sr ratio in a prostate biopsy sample prepared and analysed as described in Example 1 does not exceed 250, prostate carcinoma with an accuracy of 98±2% can be diagnosed. The sensitivity and specificity of the Ca/Sr ratio based test is 91±9% and 100-3%, respectively.

Example 39

Using the Zn/Mn Mass Fraction Ratio to Establish Prostate Condition

Figure 17:
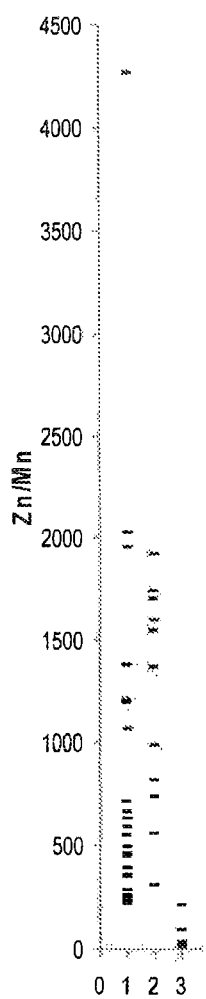
FIG. 17 shows individual data sets for Zn/Mn mass fraction ratio in samples of normal (1), benign hyperplastic (2) and cancerous prostate tissue (3).

The Zn/Mn mass fraction ratio was found to be significantly different in most cancerous prostate tissues as compared to normal and benign hyperplastic tissues (Example 8, Table 2). The upper limit for Zn/Mn mass fraction ratio on dry mass basis in cancerous prostate tissue was determined to be M+3SD (M—arithmetic mean, SD—standard deviation) or 170 (FIG. 17).

If PCa needs to be discriminated from normal and BPH tissue and if the Zn/Mn ratio in a prostate biopsy sample prepared and analysed as described in Example 1 does not exceed 170, prostate carcinoma with an accuracy of 98±2% can be diagnosed. The sensitivity and specificity of the Zn/Mn ratio based test is 91±9% and 100-3%, respectively.

Example 40

Using the [(Zn*Ca*Mg*Cd)/(Si*Br*Al*Ba)]*1000 Mass Fraction Ratio Combination to Establish Prostate Condition The [(Zn*Ca*Mg*Cd)/(Si*Br*Al*Ba)]*1000 mass fraction ratio combination was found to be significantly different in most cancerous prostate tissues as compared to normal and benign hyperplastic tissues. The upper limit for [(Zn*Ca*Mg*Cd)/(Si*Br*Al*Ba)]*1000 mass fraction ratio combination on dry mass basis in cancerous prostate tissue was determined to be M+60SD (M—arithmetic mean, SD—standard deviation) or 100 000 (FIG. 18).

If PCa needs to be discriminated from normal and BPH tissue and if the [(Zn*Ca*Mg*Cd)/(Si*Br*Al*Ba)]*1000 mass fraction ratio combination in a prostate biopsy sample prepared and analysed as described in Example 1 does not exceed 100 000, prostate carcinoma with an accuracy of 100-2% can be diagnosed. The sensitivity and specificity of the [(Zn*Ca*Mg*Cd)/(Si*Br*Al*Ba)]*1000 mass fraction ratio combination based test is 100-10% and 100-3%, respectively.

Example 41

Using the Normalized Mass Fraction Ratio Combinations of Ag, Al, Ba, Bi, Br, Ca, Cd, Ce, Co, Cr, Cs, Cu, Hg, K, Li, Mg, Mn, Na, Ni, P, Pb, Rb, S, Sb, Se, Si, Sr and Zn to Establish Prostate Condition from the Prostate Tissue Samples Mass fraction levels of the elements can be normalized to the reference levels of same elements. Further, combination of normalized mass fraction ratios can be used to diagnose prostate condition. To illustrate this the normalized mass fraction levels for 27 elements were calculated as mass fraction of the element divided by the median value of the mass fraction of the same element in the tissue samples taken from normal individuals.

Figure 19:
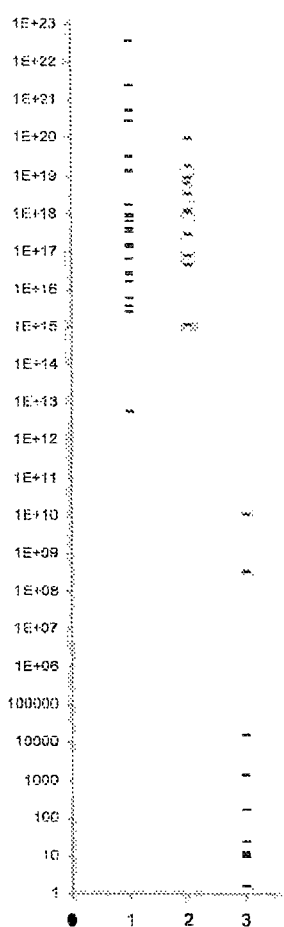
FIG. 19 shows individual data sets for [(Ca*Cd*Co*Hg*K*Mg*Na*P*Rb*S*Se*Zn)/(Ag*Al*Ba*Bi*Br*Ce*Cr*Cs*Cu*Li*Mn*Ni*Pb*Sb*Si*Sr)]*$10^{18}$ in samples of normal (1), benign hyperplastic (2) and cancerous prostate tissue (3).

The following combination of normalised mass fraction ratios [($Ca_n$*$Cd_n$*$Co_n$*$Hg_n$*$K_n$*$Mg_n$*$Na_n$*$P_n$*$Rb_n$*$S_n$*$Se_n$*$Zn_n$)/($Ag_n$*$Al_n$*$Ba_n$*$Bi_n$*$Br_n$*$Ce_n$*$Cr_n$*$Cs_n$*$Cu_n$*$Li_n$*$Mn_n$*$Ni_n$*$Pb_n$*$Sb_n$*$Si_n$*$Sr_n$)]*$10^{18}$ was found to be significantly different in most cancerous prostate tissues as compared to normal and benign hyperplastic tissues. The upper limit for [($Ca_n$*$Cd_n$*$Co_n$*$Hg_n$*$K_n$*$Mg_n$*$Na_n$*$P_n$*$Rb_n$*$S_n$*$Se_n$*$Zn_n$)/($Ag_n$*$Al_n$*$Ba_n$*$Bi_n$*$Br_n$*$Ce_n$*$Cr_n$*$Cs_n$*$Cu_n$*$Li_n$*$Mn_n$*$Ni_n$*$Pb_n$*$Sb_n$*$Si_n$*$Sr_n$)]*$10^{18}$ combination of normalised mass fraction ratios on dry mass basis in cancerous prostate tissue was determined to be 100 000 000 000 (FIG. 19).

If PCa needs to be discriminated from normal and BPH tissue and if the [($Ca_n$*$Cd_n$*$Co_n$*$Hg_n$*$K_n$*$Mg_n$*$Na_n$*$P_n$*$Rb_n$*$S_n$*$Se_n$*$Zn_n$)/($Ag_n$*$Al_n$*$Ba_n$*$Bi_n$*$Br_n$*$Ce_n$*$Cr_n$*$Cs_n$*$Cu_n$*$Li_n$*$Mn_n$*$Ni_n$*$Pb_n$*$Sb_n$*$Si_n$*$Sr_n$)]*$10^{18}$ ratio in a prostate biopsy sample prepared and analysed as described in Example 1 does not exceed 100 000 000 000, prostate carcinoma with an accuracy of 100-2% can be diagnosed. The sensitivity and specificity of the [($Ca_n$*$Cd_n$*$Co_n$*$Hg_n$*$K_n$*$Mg_n$*$Na_n$*$P_n$*$Rb_n$*$S_n$*$Se_n$*$Zn_n$)/($Ag_n$*$Al_n$*$Ba_n$*$Bi_n$*$Br_n$*$Ce_n$*$Cr_n$*$Cs_n$*$Cu_n$*$Li_n$*$Mn_n$*$Ni_n$*$Pb_n$*$Sb_n$*$Si_n$*$Sr_n$)]*$10^{18}$ ratio based test is 100-10% and 100-3%, respectively.

Example 42

Using the Normalized Mass Fraction Ratio Combinations of Ag, Al, Au, B, Ba, Bi, Br, Ca, Cd, Ce, Co, Cr, Cs, Cu, Dy, Er, Fe, Gd, Hg, Ho, K, La, Li, Mg, Mn, Na, Nd, Ni, P, Pb, Pr, Rb, S, Sb, Sc, Se, Si, Sm, Sr, Th, Tl, U, Y, Zn and Zr to Establish Prostate Condition from the Prostate Tissue Samples Mass fraction levels of the elements can be normalized to the reference levels of same elements. Further, combination of normalized mass fraction ratios can be used to diagnose prostate condition. To improve the diagnostic value of the normalized mass fraction ratio prostate cancer test the number of elements in the combination can be increased. To illustrate this the normalized mass fraction levels for 45 elements were calculated as mass fraction of the element taken from the list Ag, Al, Au, B, Ba, Bi, Br, Ca, Cd, Ce, Co, Cr, Cs, Cu, Dy, Er, Fe, Gd, Hg, Ho, K, La, U, Mg, Mn, Na, Nd, Ni, P, Pb, Pr, Rb, S, Sb, Sc, Se, Si, Sm, Sr, Th, Tl, U, Y, Zn and Zr and divided by the median value of the mass fraction of the same element in the tissue samples taken from normal individuals.

Figure 20:
FIG. 20 shows individual data sets for [(Ca*Cd*Co*Hg*K*Mg*Na*P*Rb*S*Sc*Se*Zn)/(Ag*Al*Au*B*Ba*Bi*Br*Ce*Cr*Cs*Cu*Dy*Er*Fe*Gd*Ho*La*Li*Mn*Nd*Ni*Pb*Pr*Sb*Si*Sm*Sr*Th*Tl*U*Y*Zr)]*$10^{34}$ in samples of normal (1), benign hyperplastic (2) and cancerous prostate tissue (3).

The $[(Ca_n*Cd_n*Co_n*Hg_n*K_n*Mg_n*Na_n*P_n*Rb_n*S_n*Sc_n*Se_n*Zn_n)/(Ag_n*Al_n*Au_n*B_n*Ba_n*Bi_n*Br_n*Ce_n*Cr_n*Cs_n*Cu_n*Dy_n*Er_n*Fe_n*Gd_n*Ho_n*La_n*Li_n*Mn_n*Nd_n*Ni_n*Pb_n*Pr_n*Sb_n*Si_n*Sm_n*Sr_n*Th_n*Tl_n*U_n*Y_n*Zr_n)]*10^{34}$ mass fraction ratio combination was found to be significantly different in most cancerous prostate tissue samples as compared to normal and benign hyperplastic tissue samples. The diagnostic window, i.e. the gap between the lowest normalized mass fraction ratio combination from BPH group and the highest normalized mass fraction ratio combination from the prostate cancer group, has increased to five orders of magnitude (FIG. 20). The upper limit for $[(Ca_n*Cd_n*Co_n*Hg_n*K_n*Mg_n*Na_n*P_n*Rb_n*S_n*Sc_n*Se_n*Zn_n)/(Ag_n*Al_n*Au_n*B_n*Ba_n*Bi_n*Br_n*Ce_n*Cr_n*Cs_n*Cu_n*Dy_n*Er_n*Fe_n*Gd_n*Ho_n*La_n*Li_n*Mn_n*Nd_n*Ni_n*Pb_n*Pr_n*Sb_n*Si_n*Sm_n*Sr_n*Th_n*Tl_n*U_n*Y_n*Zr_n)]*10^{34}$ normalized mass fraction ratio combination on dry mass basis in cancerous prostate tissue was determined to be $10^{24}$ (FIG. 20).

If PCa needs to be discriminated from normal and BPH tissue and if the $[(Ca_n*Cd_n*Co_n*Hg_n*K_n*Mg_n*Na_n*P_n*Rb_n*S_n*Sc_n*Se_n*Zn_n)/(Ag_n*Al_n*Au_n*B_n*Ba_n*Bi_n*Br_n*Ce_n*Cr_n*Cs_n*Cu_n*Dy_n*Er_n*Fe_n*Gd_n*Ho_n*La_n*Li_n*Mn_n*Nd_n*Ni_n*Pb_n*Pr_n*Sb_n*Si_n*Sm_n*Sr_n*Th_n*Tl_n*U_n*Y_n*Zr_n)]*10^{34}$ normalised mass fraction ratio combination in a prostate biopsy sample prepared and analyzed as described in Example 1 does not exceed $10^{24}$, prostate carcinoma with an accuracy of 100-2% can be diagnosed. The sensitivity and specificity of the $[(Ca_n*Cd_n*Co_n*Hg_n*K_n*Mg_n*Na_n*P_n*Rb_n*S_n*Sc_n*Se_n*Zn_n)/(Ag_n*Al_n*Au_n*B_n*Ba_n*Bi_n*Br_n*Ce_n*Cr_n*Cs_n*Cu_n*Dy_n*Er_n*Fe_n*Gd_n*Ho_n*La_n*Li_n*Mn_n*Nd_n*Ni_n*Pb_n*Pr_n*Sb_n*Si_n*Sm_n*Sr_n*Th_n*Ti_n*U_n*Y_n*Zr_n)]*10^{34}$ normalized mass fraction ratio combination based test is 100-10% and 100-3%, respectively.

Example 43

Identification of Cancer Biomarkers in Expressed Prostatic Secretion Using Inductively Coupled Plasma Mass Spectrometry (ICP-MS) and Inductively Coupled Atomic Emission Spectrometry (ICP-AES)

Equipment:

Inductively coupled plasma mass spectrometry instrument Agilent 7500c.

Specimen:

Expressed Prostatic Secretion samples (EPS) from patients with Benign Prostate Hyperplasia (BPH) and low-grade prostate adenocarcinoma (PCa) and EPS samples from healthy volunteers were obtained by transrectal prostate massage. The presence or absence of cancer was confirmed by Digital Rectal Examination (DRE), TransRectal Ultrasound Imaging (TRUSI) and microscopic analysis of tissue morphology in biopsies obtained from the same patients, where prescribed by the referring physician.

Reagents:

HNO3 (nitric acid 65% for analysis, max. 0.005 ppm Hg, GR, ISO, Merck), $H_2O_2$ (hydrogen peroxide pure for analysis, Merck), ICP-MS standards NCSZC73013 (NCS Certified Reference Material), BCR063R (Community Bureau of Reference of the European Comission) and IRMBD151 (LGC Standards, Weisel, Germany).

Protocol:

0.5 mL of $HNO_3$ was added to freeze-dried EPS samples and the samples were left over night at room temperature. After that 0.25 mL of $HNO_3$ and 0.15 mL of $H_2O_2$ were added to the samples and placed in water bath at 95° C. for 30 min. The heat-treated samples were cooled down to the room temperature; the soluble fraction was diluted with deionized water to 15 mL and transferred to a plastic measuring bottle. Simultaneously, the same procedure was performed on a sample containing no EPS fluid, and the resultant solution was used as a blank sample. All samples were analyzed by Inductively Coupled Plasma Mass Spectrometry and Inductively Coupled Plasma Atomic Emission Spectrometry.

The spectrometer parameters and the main parameters of ICP-MS measurements: auxiliary air flow rate—0.9 L/min, nebulizer flow rate—0.9 L/min, sample update—0.8 mL/min. The spectrometer parameters for ICP-AES measurements: generator output power 1,500 W.

Results:

The content of Al, Cd, Cs, Mn, Ni, Rb, S, Se and Si in EPS was analyzed by ICP-MS. The content of Na, Mg, P, S, K, Ca, Fe, Cu, Zn and Ba in EPS was analyzed by ICP-AES.

Statistically significant differences in mass fraction levels of 18 chemical elements (Table 11) were found in samples derived from low grade cancerous, benign hyperplastic and normal EPS.

Differences in mass fraction levels of these elements can be used for diagnosis and therapeutic purpose. The data in Table 5 allow evaluating the importance of the individual chemical element content information for the diagnosis of clinical prostate cancer (PCa).

TABLE 11

Comparison of median values of chemical element mass fractions (mg · kg$^{-1}$, dry mass basis) in normal, benign hyperplastic (BPH) and low grade cancerous (PCa) EPS.

|    | Normal | BPH    | PCa    | Normal | BPH/Normal | PCa/PCa/BPH |
|----|--------|--------|--------|--------|------------|-------------|
| Al | 29.20  | 13.06  | 91.21  | 0.4    | 3.1        | 7.0         |
| Ba | 1.12   | 0.42   | 3.23   | 0.4    | 2.9        | 7.8         |
| Ca | 9989   | 9729   | 14000  | 1.0    | 1.4        | 1.4         |
| Cd | 0.04   | 0.04   | 0.03   | 1.0    | 0.9        | 0.9         |
| Cs | 0.10   | 0.08   | 0.09   | 0.9    | 0.9        | 1.1         |
| Cu | 6.24   | 5.27   | 5.83   | 0.8    | 0.9        | 1.1         |
| Fe | 25.68  | 27.54  | 24.38  | 1.1    | 0.9        | 0.9         |
| K  | 33500  | 29367  | 48000  | 0.9    | 1.4        | 1.6         |
| Mg | 4644   | 4549   | 6500   | 1.0    | 1.4        | 1.4         |
| Mn | 0.50   | 0.93   | 1.58   | 1.8    | 3.1        | 1.7         |
| Na | 41286  | 51010  | 47000  | 1.2    | 1.1        | 0.9         |
| Ni | 0.43   | 0.83   | 0.73   | 1.9    | 1.7        | 0.9         |
| P  | 3350   | 3800   | 4400   | 1.1    | 1.3        | 1.2         |
| Rb | 40.75  | 30.93  | 47.66  | 0.8    | 1.2        | 1.5         |
| S  | 5809   | 6400   | 10521  | 1.1    | 1.8        | 1.6         |
| Se | 1.24   | 1.26   | 1.97   | 1.0    | 1.6        | 1.6         |
| Si | 84.32  | 105.4  | 110.0  | 1.3    | 1.3        | 1.0         |
| Zn | 5135   | 4100   | 8000   | 0.8    | 1.6        | 2.0         |

Example 44

Determination of Normalized Mass Fraction Levels of Elements in Normal, BPH and Low Grade Adenocarcinoma EPS Mass fraction levels of the elements can be normalized to the reference levels of same elements. In the Table 12 mass fraction ratios of 18 elements relative to reference levels of the same elements are presented. Reference levels in this example represent mean level values derived from the group of 10 EPS samples from verified healthy volunteers. Anybody skilled in the field can appreciate that corresponding reference levels must be determined for different patient populations.

TABLE 12

Mean mass fraction levels of elements normalized to the reference levels of the same elements in normal, BPH and low grade adenocarcinomatous EPS.

| | Example Reference levels, mg/kg dry mass basis | Normal | BPH | Pca | BPH/ Normal | PCa/ Normal | PCa/BPH |
|---|---|---|---|---|---|---|---|
| Al | 33.89 | 0.9 | 1.1 | 2.6 | 1.1 | 2.6 | 2.4 |
| Ba | 4.27 | 1.0 | 1.1 | 3.3 | 1.1 | 3.3 | 3.1 |
| Ca | 9528 | 1.1 | 1.0 | 1.5 | 1.0 | 1.5 | 1.5 |
| Cd | 0.13 | 0.9 | 0.7 | 0.5 | 0.7 | 0.5 | 0.8 |
| Cs | 0.12 | 0.9 | 0.7 | 1.1 | 0.7 | 1.1 | 1.6 |
| Cu | 7.31 | 1.0 | 1.2 | 1.3 | 1.2 | 1.3 | 1.1 |
| Fe | 44.66 | 0.9 | 1.4 | 1.0 | 1.4 | 1.0 | 0.8 |
| K | 32402 | 1.1 | 1.0 | 1.6 | 1.0 | 1.6 | 1.7 |
| Mg | 4225 | 1.1 | 1.0 | 1.6 | 1.0 | 1.6 | 1.5 |
| Mn | 0.94 | 1.0 | 1.8 | 1.5 | 1.8 | 1.5 | 0.8 |
| Na | 39362 | 1.0 | 1.5 | 1.5 | 1.5 | 1.5 | 1.0 |
| Ni | 0.74 | 0.9 | 2.6 | 1.5 | 2.6 | 1.5 | 0.6 |
| P | 3901 | 0.9 | 1.1 | 1.0 | 1.1 | 1.0 | 0.9 |
| Rb | 40.15 | 1.1 | 0.8 | 1.4 | 0.8 | 1.4 | 1.8 |
| S | 6471 | 1.0 | 1.1 | 1.6 | 1.1 | 1.6 | 1.5 |
| Se | 1.52 | 1.0 | 0.9 | 1.4 | 0.9 | 1.4 | 1.6 |
| Si | 75.41 | 0.9 | 1.6 | 2.6 | 1.6 | 2.6 | 1.6 |
| Zn | 4870 | 1.0 | 0.8 | 1.7 | 0.8 | 1.7 | 2.1 |

The data in the Table 12 allow evaluating the importance of normalized mass fraction levels for the diagnosis of PCa. To illustrate this further examples are given.

Example 45

Establishing the Prostate Condition Using the Additive Index Based on the Normalized Mass Fractions of Ca, K, Mg and Zn in EPS Further, based on the normalized mass fractions of the elements determined as described in Example 44 the Additive Index (AI) of prostate condition can be calculated, as exemplified here:

$$AI=(Ca_n+K_n+Mg_n+Zn_n)-4$$

where $Ca_n$, $K_n$, $Mg_n$, $Zn_n$ represent normalized values, i.e. mass fractions of Ca, K, Mg and Zn in EPS samples of the subject, divided by the reference levels of the same elements. Additive Index was found to be significantly different in most cancerous EPS as compared to normal and benign hyperplastic EPS (Table 13).

Figure 21:
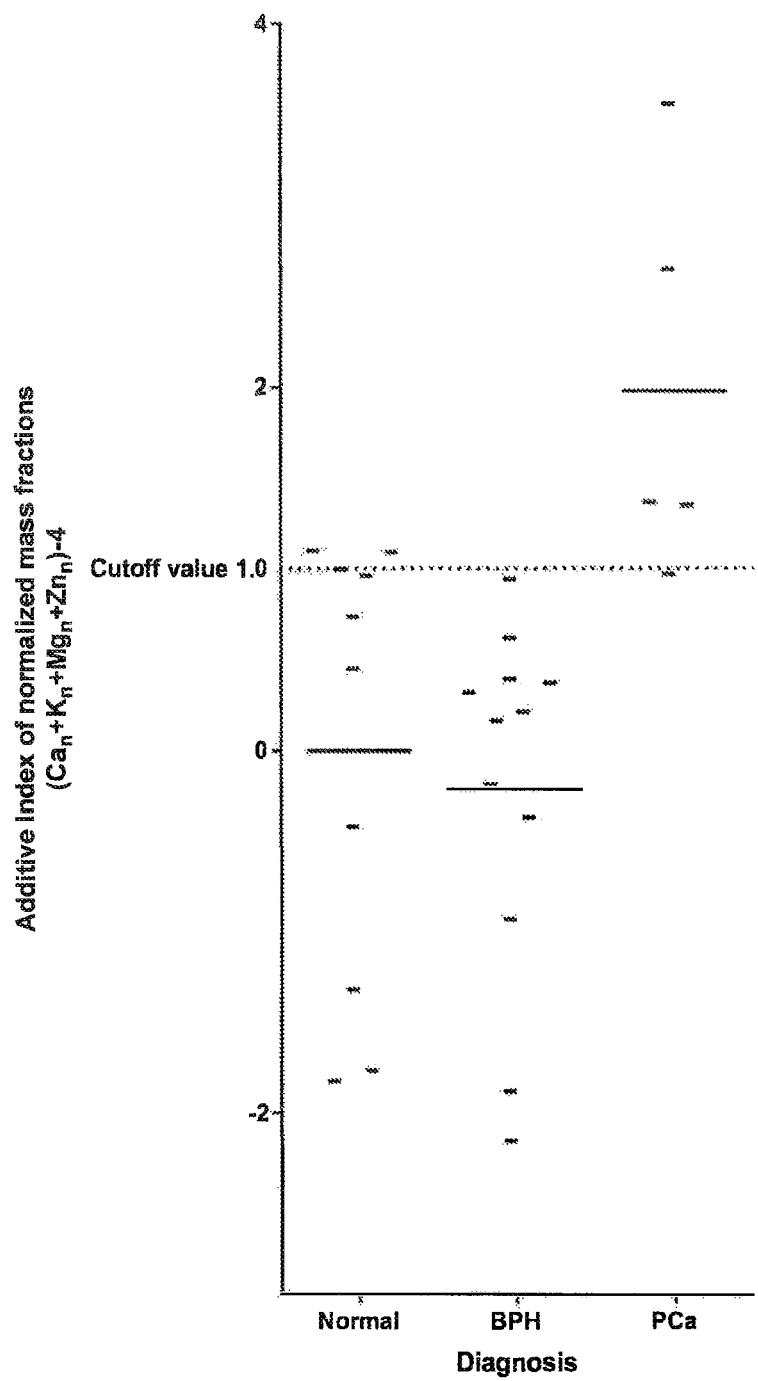
FIG. 21 shows individual data sets for normalized mass fraction additive indices of four selected elements in samples of normal, benign hyperplastic and cancerous EPS.

If PCa needs to be discriminated from normal and BPH and if the Additive Index in the EPS sample prepared and analyzed as described in Example 43 exceeds the value of 1.0, prostate carcinoma with an accuracy exceeding 95% can be diagnosed (FIG. 21).

TABLE 13

Comparison of the Additive Indices between the diagnostic groups.

| | Normal | BPH | PCa |
|---|---|---|---|
| Mean | −3e−007 | −0.21 | 2.0 |
| Std. Deviation | 1.2 | 1.0 | 1.1 |
| Std. Error of Mean | 0.39 | 0.28 | 0.49 |
| Lower 95% CI of mean | −0.9 | −0.8 | 0.6 |
| Upper 95% CI of mean | 0.9 | 0.4 | 3.3 |

Example 46

Establishing the Prostate Condition Using the Multiplicative Index Based on the Normalized Mass Fractions of Ca, K, Mg and Zn in EPS Further, based on the normalized mass fractions of the elements determined as described in Example 44 the Multiplicative Index (MI) of prostate condition can be calculated, as exemplified here:

$$MI=(Ca_n*K_n*Mg_n*Zn_n)/4$$

where $Ca_n$, $K_n$, $Mg_n$, $Zn_n$ represent mass fractions of Ca, K, Mg and Zn in EPS of the subject normalised to the reference levels. Multiplicative Index was found to be significantly different in most cancerous EPS as compared to normal and benign hyperplastic EPS (Table 14).

Figure 22:
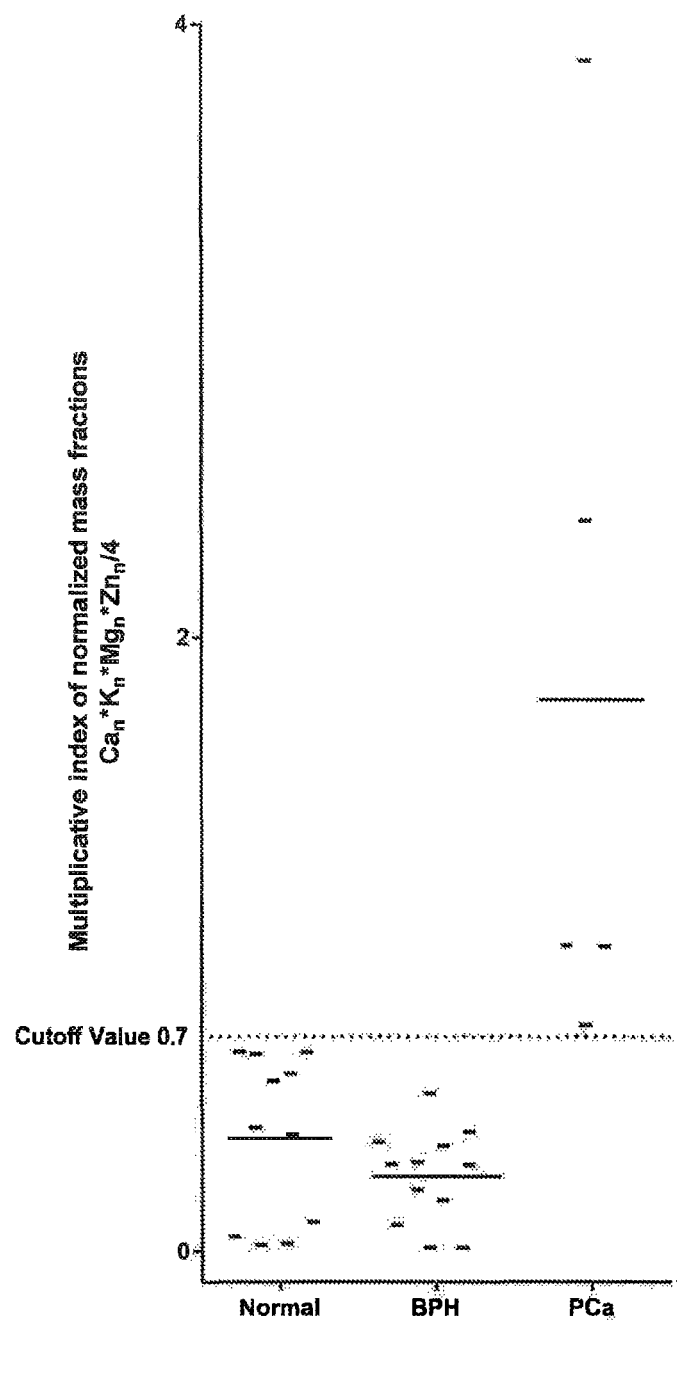
FIG. 22 shows individual data sets for normalized mass fraction multiplicative indices of four selected elements in samples of EPS from normal, benign hyperplastic and cancerous patients.

If PCa needs to be discriminated from normal and BPH and if the Multiplicative Index in the EPS sample prepared and analysed as described in Example 43 exceeds the value of 0.7, prostate carcinoma with an accuracy exceeding 99% can be diagnosed (FIG. 22).

TABLE 14

Comparison of the Multiplicative Indices between the diagnostic groups.

| | Normal | BPH | PCa |
|---|---|---|---|
| Mean | 0.4 | 0.2 | 1.8 |
| Std. Deviation | 0.27 | 0.16 | 1.3 |
| Std. Error of Mean | 0.08 | 0.04 | 0.6 |
| Lower 95% CI of mean | 0.2 | 0.1 | 0.1 |
| Upper 95% CI of mean | 0.5 | 0.3 | 3.5 |

Example 47

Establishing the Prostate Condition Using the Multiplicative Index Based on the Normalized Mass Fractions of Ca, K, Mg, Rb, S and Zn in EPS Further, based on the normalized mass fractions of the elements determined as described in Example 44 the 6-element Multiplicative Index (MI/6) of prostate condition can be calculated, as exemplified here:

$$MI/6=(Ca_n*K_n*Mg_n*Rb_n*S_n*Zn_n)6$$

where $Ca_n$, $K_n$, $Mg_n$, $Rb_n$, $S_n$ and $Zn_n$ represent mass fractions of Ca, K, Mg, Rb, S and Zn in EPS of the subject normalised to the reference levels. Multiplicative Index was found to be significantly different in most cancerous EPS as compared to normal and benign hyperplastic EPS (Table 15).

Figure 23:
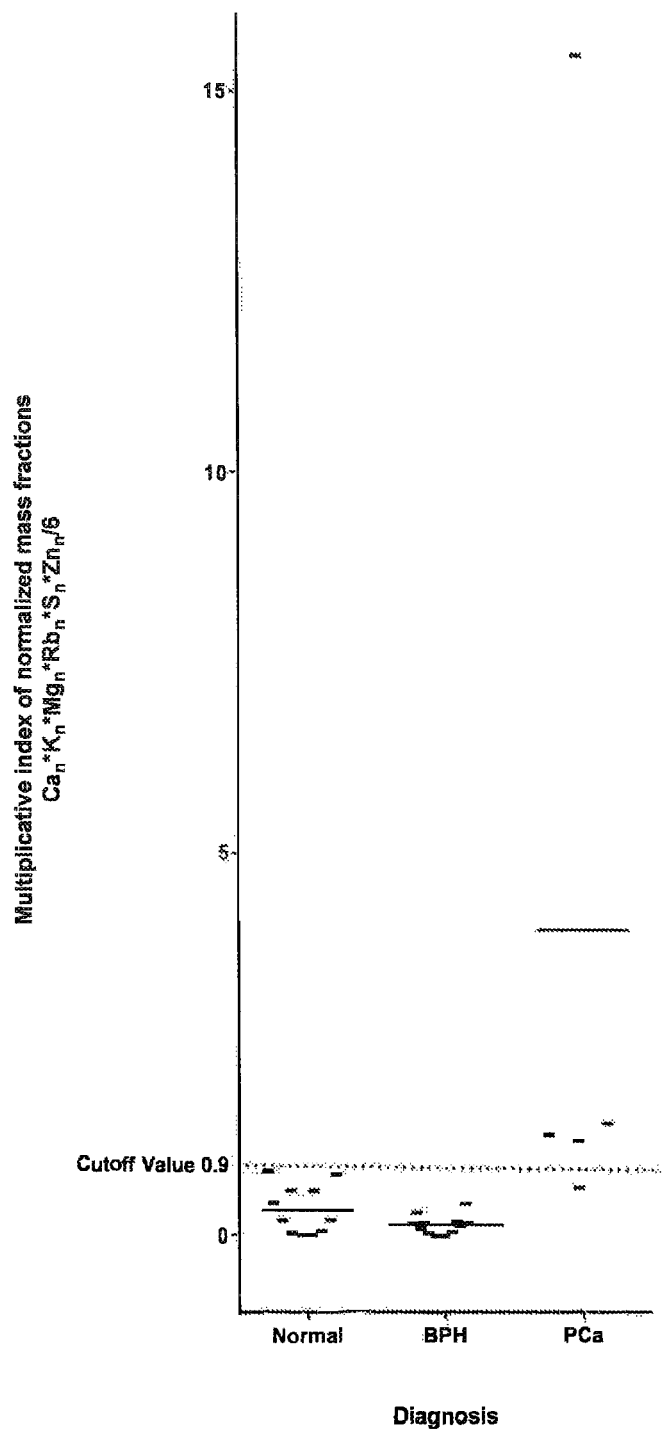
FIG. 23 shows individual data sets for normalized mass fraction multiplicative indices of six selected elements in samples of EPS from normal, benign hyperplastic and cancerous patients.

If PCa needs to be discriminated from normal and BPH and if the Multiplicative Index in the EPS sample prepared and analysed as described in Example 43 exceeds the value of 0.9, prostate carcinoma with an accuracy exceeding 95% can be diagnosed (FIG. 23).

TABLE 15

Comparison of the Multiplicative Indices between the diagnostic groups.

|  | Normal | BPH | Pca |
|---|---|---|---|
| Mean | 0.3 | 0.2 | 4.1 |
| Std. Deviation | 0.3 | 0.13 | 6.4 |
| Std. Error of Mean | 0.1 | 0.04 | 2.9 |
| Lower 95% CI of mean | 0.13 | 0.07 | −3.9 |
| Upper 95% CI of mean | 0.6 | 0.2 | 12 |

Example 48

Identification of Cancer Biomarkers in Expressed Prostatic Secretion Using Energy Dispersive X-Ray Fluorescence (EDXRF)

Equipment and Method:

EDXRF spectrometer consisted of an annular $^{109}$Cd source with an activity of 2.56 GBq, a 25 mm$^2$ Si(Li) detector and portable multichannel analyzer combined with a PC. Its resolution was 270 eV at the 5.9 keV line of 55Fe-source. The duration of the Zn measurements together with Br, Fe, Rb, and Sr was 60 min. The intensity of Kα-line of Br. Fe, Rb, Sr, and Zn for samples and standards was estimated on the basis of calculating the total area of the corresponding photopeak in the spectra. The element content was calculated by comparing intensities of Kα-lines for samples and standards.

Specimen:

Expressed Prostatic Secretion samples (EPS) from patients with Benign Prostate Hyperplasia (BPH) and adenocarcinoma (PCa) and EPS samples from healthy volunteers were obtained by transrectal prostate massage. The presence or absence of cancer was confirmed by Digital Rectal Examination (DRE), Ultrasound Imaging (TRUSI) and microscopic analysis of tissue morphology in biopsies obtained from the same patients, where prescribed by the referring physician.

Sample Preparation:

20 μl of the EPS sample were placed on a backing comprised of a thin film of transparent polymeric material (Dacron, Mylar, polyethylene or similar, thickness <10 μm). The drop of a sample was freeze-dried on a backing until the constant mass.

Results:

The content of Zn, Br, Fe, Rb, and Sr in EPS obtained from 32 healthy volunteers, 23 BPH patients and 10 prostate adenocarcinoma patients was analyzed by EDXRF.

Differences in mass fraction levels of Zn and Rb were found to be statistically significant in samples derived from cancerous, benign hyperplastic and normal EPS samples.

Combination of these elements can be used for diagnosis and therapeutic purpose. The product of mass fraction levels of Rb and Zn divided by ten, as expressed by the following formula: (Rb*Zn)/10 was found to be the most informative marker of prostate cancer. The data in Table 16 allow evaluating the importance of the combination of mass fraction levels of Rb and Zn for the diagnosis of clinical prostate cancer (PCa).

Figure 24:
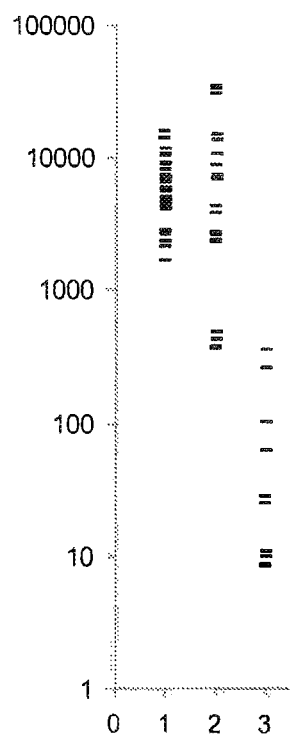
FIG. 24. Individual data sets for product index (Rb*Zn)/10 obtained from the EPS samples from healthy (1), benign hypertrophic (2) and cancerous individuals (3).

If PCa needs to be discriminated from normal and BPH and if the Product index (Rb*Zn)/10 in the EPS sample prepared and analysed as described in Example 48 exceeds the value of 350, prostate carcinoma with an accuracy exceeding 98% can be diagnosed (FIG. 24).

TABLE 16

Parameters of the importance (sensitivity, specificity and accuracy) of the Product index (Rb × Zn)/10 in the samples of expressed prostatic secretion for the diagnosis of PCa (an estimation is made for "Pca" or "Intact and BPH").

| Upper limit for PCa | Sensitivity, % | Specificity, % | Accuracy, % |
|---|---|---|---|
| <350 | 100-10 | 100-2 | 100-2 |

The invention claimed is:

1. A method of diagnosing a prostate condition in a subject, comprising:
measuring, in a sample obtained from a subject, levels of plurality of constituents comprising Ag, Al, Au, B, Ba, Bi, Br, Ca, Cd, Ce, Co, Cr, Cs, Cu, Dy, Er, Fe, Gd, Hg, Ho, K, La, Li, Mg, Mn, Nd, Ni, Pb, Pr, Rb, S, Sb, Sc, Se, Si, Sm, Tb, Th, Tl, U, Y, Zr, Na, P, S, Sr and Zn;
determining a ratio of a combination of plurality of constituents, wherein the ratio is selected from the group consisting of Ca/Fe, Mg/Al, Ca/Cu, Mg/Cu, Zn/Cu, Ca/Mn, Ca/Al, Ca/Ba, Zn/Mn, Ca/P, Ca/Si, Ca/Sr, (Ca/Cu)*(Mg/Cu), (Ca/Cu)*(Zn/Cu), (Mg/Cu)*(Zn/Cu), (Ca*Mg*Zn)/(Al*Bi*Cu), (Ca*Mg*Zn)/(Mn*Bi*Se), (Zn*Ca*Mg*Cd)/(Si*Br*Al*Ba), (Zn*Rb)/10, (Ca$_n$*Cd$_n$*Co$_n$*Hg$_n$*K$_n$*Mg$_n$*Na$_n$*P$_n$*Rb$_n$*S$_n$*Sc$_n$*Se$_n$*Zn$_n$)/(Ag$_n$*Al$_n$*Au$_n$*B$_n$*Ba$_n$*Bi$_n$*Br$_n$*Ce$_n$*Cr$_n$*Cs$_n$*Cu$_n$*Dy$_n$*Er$_n$*Fe$_n$*Gd$_n$*Ho$_n$*La$_n$*Li$_n$*Mn$_n$*Nd$_n$*Ni$_n$*Pb$_n$*Pr$_n$*Sb$_n$*Si$_n$*Sm$_n$*Sr$_n$*Th$_n$*Tl$_n$*U$_n$*Y$_n$*Zr$_n$), (Ca$_n$*Cd$_n$*Co$_n$*Hg$_n$*K$_n$*Mg$_n$*Na$_n$*P$_n$*Rb$_n$*S$_n$*Se$_n$*Zn$_n$)/(Ag$_n$*Al$_n$*Ba$_n$*Bi$_n$*Br$_n$*Ce$_n$*Cr$_n$*Cs$_n$*Cu$_n$*Li$_n$*Mn$_n$*Ni$_n$*Pb$_n$*Sb$_n$*Si$_n$*Sr$_n$), (Ca$_n$*K$_n$*Mg$_n$*Rb$_n$*S$_n$*Zn$_n$)/6, (Ca$_n$*K$_n$*Mg$_n$*Zn$_n$)/4 and (Ca$_n$+K$_n$+Mg$_n$+Zn$_n$)−4, wherein $_n$ indicates a normalized level, and wherein the sample is selected from the group consisting of a prostatic fluid, an expressed prostatic secretion and a seminal fluid; and
comparing the ratio of levels of the combination of plurality of constituents in the sample with control levels of the same combination of plurality of constituents, in which a difference between the combinations is indicative of the prostate condition, wherein the condition is selected from the group consisting of prostate cancer and benign prostatic hyperplasia.

2. A method according to claim 1, in which the bodily fluid sample is expressed prostatic secretion.

3. A method according to claim 1, in which the bodily fluid sample is seminal fluid.

4. A method according to any one of claims 1, 2, and 3, in which the condition is prostate cancer.

5. A method according to any one of claims 1, 2, and 3 in which the condition is benign prostatic hyperplasia.

6. The method of claim 1, wherein the measuring step is achieved by at least two different detection methods.

7. The method of claim 6, wherein the at least two different detection methods comprise Inductively-coupled plasma mass spectrometry (ICP-MS) and Inductively-coupled plasma atomic emission spectroscopy (ICP-AES).

* * * * *